US012728182B2

(12) United States Patent
Zhang et al.

(10) Patent No.: US 12,728,182 B2
(45) Date of Patent: Sep. 8, 2026

(54) MEDICAL MATERIAL AND PRODUCT AND PREPARATION METHOD THEREOF

(71) Applicant: Peking University School of Stomatology, Beijing (CN)

(72) Inventors: Xuehui Zhang, Beijing City (CN); Xuliang Deng, Beijing City (CN); Jia Song, Beijing City (CN); Yunyang Bai, Beijing City (CN); Yang Liu, Beijing City (CN); Yanhui Lu, Beijing City (CN); Liping Wu, Beijing City (CN)

(73) Assignee: PEKING UNIVERSITY SCHOOL OF STOMATOLOGY, Beijing (CN)

( * ) Notice: Subject to any disclaimer, the term of this patent is extended or adjusted under 35 U.S.C. 154(b) by 300 days.

(21) Appl. No.: 18/476,760

(22) Filed: Sep. 28, 2023

(65) Prior Publication Data

US 2024/0108783 A1 Apr. 4, 2024

(30) Foreign Application Priority Data

Sep. 30, 2022 (CN) ......................... 202211206420.6
Sep. 30, 2022 (CN) ......................... 202211206527.0
Sep. 30, 2022 (CN) ......................... 202211207278.7
Jul. 24, 2023 (CN) ......................... 202310906012.X

(51) Int. Cl.

| | |
|---|---|
| ***A61L 26/00*** | (2006.01) |
| ***D04H 1/413*** | (2012.01) |
| ***D04H 1/4318*** | (2012.01) |
| ***D04H 1/56*** | (2006.01) |
| ***D04H 1/728*** | (2012.01) |
| ***D06C 7/00*** | (2006.01) |
| ***D06M 10/02*** | (2006.01) |
| *D06M 101/22* | (2006.01) |

(52) U.S. Cl.

CPC ....... *A61L 26/0004* (2013.01); *A61L 26/0014* (2013.01); *A61L 26/0019* (2013.01); *A61L 26/0066* (2013.01); *A61L 26/0085* (2013.01); *D04H 1/413* (2013.01); *D04H 1/4318* (2013.01); *D04H 1/56* (2013.01); *D04H 1/728* (2013.01); *D06C 7/00* (2013.01); *D06M 10/02* (2013.01); *D06M 10/025* (2013.01); *A61L 2300/102* (2013.01); *A61L 2300/404* (2013.01); *A61L 2400/12* (2013.01); *D06M 2101/22* (2013.01); *D10B 2321/042* (2013.01); *D10B 2401/13* (2013.01); *D10B 2509/022* (2013.01)

(58) Field of Classification Search

CPC ............. A61L 26/0004; A61L 26/0014; A61L 26/0019; A61L 26/0066; A61L 26/0085; D04H 1/413; D04H 1/728

See application file for complete search history.

(56) References Cited

FOREIGN PATENT DOCUMENTS

| | | | |
|---|---|---|---|
| CN | 102085457 A | | 6/2011 |
| CN | 102527262 A | | 7/2012 |
| CN | 103933873 A | | 7/2014 |
| CN | 106478149 A | | 3/2017 |
| CN | 107261205 A | * | 10/2017 |
| CN | 112870391 A | * | 6/2021 |
| CN | 102527262 B | * | 7/2021 |
| CN | 113521321 A | | 10/2021 |
| CN | 114904054 A | | 8/2022 |
| CN | 114959933 A | | 8/2022 |

OTHER PUBLICATIONS

Lukiev et al, Article, Membranes, 2021, 11, 982; (Antibacterial ferroelectric hybrid membranes fabricated via electrospinning for wound healing). (Year: 2021).*

Ying Yin et at; "A comparaitve study on the bone repair effects of two kinds of tissue regeneration membranes"; Chinese Journal of Tissue Engineering Research, 2020; vol. 24, No. 10; pp. 1515-1520. (English Abstract).

Jiani Liao et al; "Application of P(VDF-TrFE) Copolymer in Acoustic Emission Sensor"; Journal of Sensor Technology and Application; vol. 8, No. 2, Apr. 2, 2020; pp. 34-44. (English Abstract).

Yudong Hou et al; Chemical Construction and Physical Property Analysis of electronic Ceramics; Metallurgical Industry Press, Beijing; Apr. 2020; pp. 302-303.

Wang, Zhan; Fundamentals of membrane separation technology; Chemical Industry Press; 2000; pp. 15-16.

* cited by examiner

*Primary Examiner* — Mina Haghighatian

(74) *Attorney, Agent, or Firm* — HAUPTMAN HAM, LLP

(57) ABSTRACT

The present disclosure discloses a medical material and a product and preparation method thereof. The medical material comprises a ferroelectric polymer, and optionally further comprises an inorganic ferroelectric particle. The composite membrane is prepared by experiencing at least one of annealing treatment, corona poling treatment, acid treatment, and ultrasonic treatment, and the acid treatment is conducted after the annealing treatment. The present disclosure further relates to a method for treating a composite membrane to regulate an antibacterial activity.

9 Claims, 8 Drawing Sheets

Buccal
Palatal
Control Group
Ligation Group
Periodontitis Model
0.0
0.1
0.2
0.3
0.4
0.5
Control Group
Ligation Group 2W
3W
4W
Blank Group
Non-charged Group
Charged Group
Distance (mm)
Blank Group
Non-charged Group
Charged Group Charged Dense Membrane Example 1 Membrane Charged Dense Membrane Example 1 Membrane

MEDICAL MATERIAL AND PRODUCT AND PREPARATION METHOD THEREOF

CROSS-REFERENCE TO RELATED APPLICATION

The present application claims the benefit of a priority of an application for invention of patent filed in China on Sep. 30, 2022, of which the Application No. is CN202211206420.6 entitled "ANTIMICROBIAL DRESSING BASED ON FERROELECTRIC MATERIAL AND PREPARATION METHOD AND APPLICATION THEREOF"; the benefit of a priority of an application for invention of patent filed in China on Sep. 30, 2022, of which the Application No. is CN202211206527.0 entitled "TISSUE REPAIR MEMBRANE WITH AIR PERMEABILITY AND ELECTROACTIVITY AS WELL AS PREPARATION METHOD AND APPLICATION THEREOF"; the benefit of a priority of an application for invention of patent filed in China on Sep. 30, 2022, of which the Application No. is CN202211207278.7 entitled "METHOD FOR REGULATING ANTIBACTERIAL ACTIVITY AND APPLICATION THEREOF"; and the benefit of a priority of an application for invention of patent filed in China on Jul. 24, 2023, of which the Application No. is CN202310906012.X entitled "METHOD FOR IMPROVING PIEZOELECTRIC PROPERTY OF POLYLACTIC ACID FIBER MEMBRANE AND APPLICATION THEREOF", the entire contents of which are incorporated herein by reference.

TECHNICAL FIELD

The present disclosure relates to the field of biological materials, specifically to a medical material as well as a preparation method and use thereof.

BACKGROUND

Current clinical evaluations and studies have shown that there are some deficiencies in wound dressings and collagen membranes and the like commonly used on the market. For example, transparent dressings are easily adhered to wounds, have dissatisfactory antimicrobial effects, and lack a tissue regeneration-inducing activity, and currently available piezoelectric materials cannot generate electrical signals without applying external force, etc. PTFE is a barrier membrane commonly used for severe periodontitis in clinic to induce bone tissue regeneration. However, due to lacking an antimicrobial activity of PTFE, exposure after operation tends to cause infective complications, leading to a repair failure. Moreover, the tissue regeneration-inducing activity and anti-adhesion of such non-absorbable membranes to nascent soft and hard tissues are undesirable. Therefore, there is a need to develop novel antimicrobial biomaterials capable of effectively promoting regeneration of infected tissues.

From the perspective of tissue regeneration, ferroelectric polymer membranes such as polyvinylidene difluoride (PVDF) and copolymers thereof have excellent mechanical properties, high dielectric constant and electro-responsive activity, good biocompatibility and chemical stability, and non-degradability, and are widely used in tissue engineering, biomedical sensors, and medical sutures, etc. However, although polyvinylidene difluoride and copolymers thereof have an inherently spontaneous poling property and can reach the biomimetic physiological potential of human tissues to promote tissue regeneration, the existing solid-wall membranes are not breathable, leading to tissue hypoxia and necrosis in closed environments.

In order to improve the breathability of solid-wall membranes while further improving the plasticity and tissue adhesiveness of solid-wall membranes, biomimetic electroactive polymer membranes may be prepared into a porous membrane structure. The biomimetic electroactive polymer membranes with a porous structure may be widely used in the medical field, such as drug-loaded sustained-release biomaterials, medical breathable gauze and tissue engineering scaffolds, etc. because they have good mechanical properties and a controllable porous structure. Nevertheless, the porous structure inside the electroactive polymer membranes affects their poling and thus affects their piezoelectric activity.

In terms of bone regeneration and repair, numerous studies have shown that bone has piezoelectric properties, and piezoelectric materials make use of the inverse piezoelectric effect to convert the mechanical strain into an electrical signal to mimic the electrophysiological environment of the bone tissue and promote bone regeneration and repair. Previous studies have reported that polylactic acid, as an ultrasound-responsive piezoelectric material, has good mechanical properties, degradability, biocompatibility and antimicrobial properties, and has been widely used in the fields of sensors, environmental engineering and wearable devices. However, it has been found that poly(L-lactic acid) has low piezoelectric properties and cannot regulate the electrical output performance, such that it is restricted in bone defect repair and cannot adapt to the complex regulatory mechanism in the process of bone repair in the organism.

From the perspective of antimicrobial property, physical antimicrobial methods have received much attention in the field of research on antimicrobial technologies because of their advantages such as ease of use and avoidance of bacterial drug resistance caused by use of drugs. Common physical antimicrobial methods include methods such as electrical, magnetic, light, ultrasonic and thermal stimulations, of which bacteria resistance by the electrical stimulation has aroused great interest. However, common electrical stimulation methods such as loading current, external electric field and external magnetic field have obvious disadvantages such as a need of additional electric field or power supply, which is not favorable to clinical application. It has also been reported that conductive materials or piezoelectric materials are used to resist bacteria, but there are still some shortcomings such as a difficulty in how to mold piezoelectric materials, uncontrollable electric quantity, and clinical inoperability.

CN111184908A, a Chinese patent application, discloses a piezoelectric antimicrobial technology of adding a micro-nanomaterial Mxene to nano niobate to obtain an Mxene composite piezoelectric material, which is then immersed in an antimicrobial drug-containing solvent to fulfill the purposes of resisting bacteria and promoting osteoclast adhesion by relying on the antimicrobial drug. CN110237307A, a Chinese patent application, discloses a technology of resisting bacteria by piezoelectric composite materials, in which polyether-ether-ketone and niobate are dried and then blended, molded and prepared into a composite fiber material under the condition of 350° C. to 450° C., and subsequently subjected to surface treatment, immersed in an antimicrobial drug solution, etc. This technology also depends on antimicrobial drug to achieve the antimicrobial property and there are problems such as an uncertainty in antimicrobial effects.

CN107721402A, a Chinese patent application, discloses a preparation method for an antimicrobial piezoelectric material. With complicated components, the piezoelectric material realizes the antimicrobial property depending mainly on silver nitrate rather than on the electrical signal of the piezoelectric material, so there are problems about release of silver ions and instability of effects thereof and potential biosafety.

CN107721420A, a Chinese patent application, discloses an antimicrobial technology of copper ions-doped piezoelectric materials, in which niobium pentoxide, sodium carbonate, and potassium carbonate are mixed to prepare potassium-sodium niobate precursor powder, and then copper oxide is added and mixed with a binder to obtain a copper oxide-doped potassium-sodium niobate piezoelectric ceramic. CN106478149A, a Chinese patent application, discloses a piezoelectric material with antimicrobial properties, comprising potassium-sodium niobate as a main component, where the antimicrobial effect is mainly provided by polarization charges after the material is polarized. Both technologies in these two applications have the problems about a difficulty in cleaning after oil-bath polarization and potential influences of the release of copper ions or copper electrode residues on the human body. Moreover, the technology in CN106478149A does not show that the materials are effective on both Gram-negative bacteria and Gram-positive bacteria.

CN 107802878A, a Chinese patent application, discloses a modified gelatin/potassium sodium niobate composite electroactive antimicrobial biological dressing and a preparation technique thereof, in which methacrylate hydrogel as gelatin and potassium sodium niobate piezoelectric particles/potassium sodium niobate nanofibers are cured to form a membrane under the action of an initiator, and then polarized. This antimicrobial technique involves many components of materials for preparation and complicated processes including photocuring, electrospinning, sintering, etc., and also has problems about biological safety resulting from shedding of potassium sodium niobate particles caused by degradation of gelatin and monomer residues caused by incomplete curing of polymers.

The information described in the Background of the present application is merely for illustrating the general background of the present disclosure and shall not be construed to admit or imply in any way that these pieces of information constitute the prior arts known to those of ordinary skill in the art.

SUMMARY

Technical Problem

As can be appreciated from the above-mentioned studies in this field, the materials currently used for antimicrobial, anti-infectious, tissue defect repair and biomedical purposes have problems such as lack of antimicrobial activities, ease to cause an infection, tissue hypoxia and necrosis, poor tissue repair and regeneration effects, and lack of biosafety caused by residues in the preparation process of materials.

Solution to Problem

The present disclosure provides a medical material, wherein the medical material is based on a ferroelectric material, the ferroelectric material comprises a ferroelectric polymer, and optionally an inorganic ferroelectric particle (such as a ferroelectric ceramic particle), and the inorganic ferroelectric particle accounts for 0 to 20% by volume of the ferroelectric polymer, and the inorganic ferroelectric particle has a diameter of from 50 nm to 500 nm.

In some embodiments, the medical material according to the present disclosure, further comprising a porous structure in the interior.

In some embodiments, the medical material according to the present disclosure, wherein the ferroelectric polymer is at least one selected from the group consisting of polyvinylidene difluoride, polyvinylidene fluoride-hexafluoropropylene, polyvinylidene fluoride-trifluoroethylene, and polylactic acid.

In some embodiments, the medical material according to the present disclosure, wherein the inorganic ferroelectric particle comprises at least one of barium titanate, barium strontium titanate, bismuth ferrite, potassium sodium niobate, and lithium niobate.

In some embodiments, the medical material according to the present disclosure, wherein the composite membrane has a piezoelectric constant of 5 pC/N or more, and the tissue repair membrane has water vapor permeance of 500 $g/m^2 \cdot 24$ h or more at 38° C., 90% RH.

In some embodiments, the medical material according to the present disclosure, wherein the composite membrane is an antimicrobial dressing or a tissue repair membrane.

The present disclosure further provides a method for preparing a medical material, wherein the method comprises the following steps:

(1) preparing a precursor material (e.g. a composite material) from a ferroelectric polymer and optionally an inorganic ferroelectric particle and/or an inorganic pore-forming agent; and (2) subjecting the precursor material to at least one of annealing treatment, corona poling treatment, acid treatment, and optionally ultrasonic treatment, wherein the acid treatment is conducted after the annealing treatment.

The present disclosure further provides a method for preparing a medical material, wherein the method comprises the following steps:

(1) dissolving a ferroelectric polymer into an organic solvent, and optionally adding an inorganic ferroelectric particle and/or an inorganic pore-forming agent to form a ferroelectric polymer mixture;

(2) transferring the ferroelectric polymer mixture to an electrospinning syringe for electrospinning; and (3) subjecting a membrane formed after completion of spinning to drying at room temperature and then to at least one of annealing treatment, corona poling treatment, acid treatment, and ultrasonic treatment.

In some embodiments, the preparation method for the medical material according to the present disclosure, wherein the inorganic pore-forming agent comprises zinc oxide and/or calcium carbonate.

In some embodiments, the preparation method for the medical material according to the present disclosure, wherein conditions for the annealing treatment comprise treatment in air or vacuum at a temperature of 80° C. to 150° C. for 5 min to 2 h, followed by natural cooling.

In some embodiments, the preparation method for the medical material according to the present disclosure, wherein conditions for the corona poling treatment comprise polarization field strength of 0.1 kV/mm to 30 kV/mm, polarization time of 1 min to 60 min, a polarization medium being air, methyl silicone oil or vacuum, and a polarization temperature of 25° C. to 100° C.

In some embodiments, the preparation method for the medical material according to the present disclosure, wherein the acid treatment comprises treatment for 3 to 30 h with an acidic solution selected from aqueous solutions of hydrochloric acid, sulfuric acid, nitric acid, and carbonic acid, and the acidic solution has a mass percent concentration of from 1% to 50%.

In some embodiments, the preparation method for the medical material according to the present disclosure, wherein the ultrasonic treatment is low-intensity ultrasound, preferably the ultrasound has an effective sound intensity of from 0.20 to 2.50 $W/cm^2$; the ultrasound has an ultrasonic frequency of from 0.5 to 4 MHz; preferably, the ultrasound is continuous ultrasound or pulsed ultrasound.

In some embodiments, the preparation method for the medical material according to the present disclosure, wherein the method comprises:

preparing a composite material from a ferroelectric polymer, a ferroelectric ceramic particle, and an inorganic pore-forming agent; and subjecting the composite material to annealing treatment, corona poling treatment, and acid treatment, successively; or to corona poling treatment, annealing treatment, and acid treatment, successively.

In some embodiments, the method for preparing a medical material according to the present disclosure, wherein the method comprises the following steps:

(1) dissolving a ferroelectric polymer into an organic solvent to form a ferroelectric polymer mixture;

(2) adding at least one inorganic particle selected from zinc oxide, calcium carbonate, and barium titanate to the ferroelectric polymer mixture and mixing to form a dispersion;

(3) preparing a membrane from the dispersion by membrane casting to obtain a primary membrane, and immersing the primary membrane into an acidic solution for treatment to obtain a breathable polymer membrane; and (4) subjecting the breathable polymer membrane to the annealing treatment at 80° C. to 100° C. for 5 to 30 min, then to natural cooling at room temperature, and subsequently to the corona poling treatment, thereby obtaining a composite membrane with both breathability and electroactivity.

The present disclosure further provides a method for regulating an antimicrobial activity, wherein the method comprises a step of treating a ferroelectric material to regulate a charge amount of an antimicrobial material, the ferroelectric material comprises a ferroelectric polymer and optionally an inorganic ferroelectric particle and/or an inorganic pore-forming agent, and the inorganic ferroelectric particle accounts for 0 to 20% by volume of the ferroelectric polymer.

In some embodiments, the method for regulating the antimicrobial activity according to the present disclosure, wherein the ferroelectric material is subjected to annealing treatment, corona poling treatment, and acid treatment, wherein the acid treatment is conducted after the annealing treatment.

In some embodiments, the method for regulating the antimicrobial activity according to the present disclosure, wherein the antibacteria comprises broad-spectrum antibacteria against Gram-negative bacteria and Gram-positive bacteria.

The present disclosure further provides use of the above-mentioned medical material in the preparation of an anti-infective product and a biomedical product.

In some embodiments, the use according to the present disclosure, wherein the anti-infective product and the biomedical product comprise a barrier membrane for periodontitis, an infectious bone trauma repair membrane, an infectious mucosal injury repair membrane, an oral implant repair membrane, and an oral ulcer repair membrane.

Advantageous Effects of the Invention

The medical materials prepared in the present disclosure have the following advantages:

As Tissue Repair Membranes:

1. They possess both breathability and electroactivity. The water vapor permeance of the polymer membrane is controlled under the conditions of inorganic particles, acidic solution treatment, and annealing treatment.
2. They possess excellent mechanical properties and their tensile strength may reach 30 MPa, indicating that the tensile resistance of the tissue repair membrane is beneficial to its use as a biomedical product. The tissue repair membrane of the present disclosure may have a sponge-like porous structure in its surface and interior, which has greater affinity for water and blood, good hygroscopic properties, and a small surface pore diameter, e.g. medical implant materials for promoting tissue regeneration, which serves double beneficial duty of absorbing exudates and defensing against external bacteria.
3. The ferroelectric polymer used in the present disclosure has an excellent dielectric constant and good biocompatibility, and is excellent in biosafety while achieving a biomimetic effect. It may be used in the fields such as drug-loaded sustained-release biomaterials, medical breathable gauze, and tissue engineering scaffolds, and has good application prospects.

Therefore, the tissue repair membrane with both breathability and electroactivity as provided herein has excellent material properties and good tissue repair effects. It not only achieves the biomimetic level of electroactivity of human tissue, but also has breathability capable of preventing tissue hypoxia and necrosis in a closed environment. Its non-degradability and anti-adhesion properties make it better to prevent material residues. At the same time, there is no leakage of metal ions, which even avoids potential biosafety issues. Furthermore, the non-degradable property of the tissue repair membrane allows its biomimetic electroactivity to be maintained steadily and it has excellent biological reactivity, which is of great significance for further improvement of the repair and regeneration of tissue defects.

As Antimicrobial Materials:

In respect of common skin infection and periodontal infection and the like caused typically by *Staphylococcus aureus* and *Porphyromonas gingivalis*, the present disclosure demonstrates by experiments that the prepared antimicrobial materials (e.g. antimicrobial dressings) are also effective in fighting against bacteria without applying any external force, and facilitate the regeneration capacity of an infectious tissue. The effect of the BTO/P(VDF-TrFE) electroactive composite membrane on the tissue regeneration capacity is evaluated by detecting the bacteria content in tissues of mice at day 3 and day 8, comparing the skin wound healing speeds, and observing the tissue morphology with histological staining. The results show that the charged membrane exhibits better results. Immunofluorence assay further indicates that the expression of IL-6 in the High-charged group is far lower than that in other groups, suggesting that the antimicrobial material of the present disclosure has an anti-inflammatory effect, which confirms its anti-infection effect in vivo. Additionally, the active expression of CD31 and KRT5—epithelial repair-related major molecules—further verifies the capacity of the charged membrane material to effectively promote tissue regeneration.

Furthermore, the preparation method for the medical material of the present disclosure has the following advantages:

1. In the preparation of a porous membrane material, a step of acid treatment is carried out and the acid dissolution method is adopted, where both the inorganic pore-forming agent and inorganic piezoelectric particles will be dissolved out with the dissolution of acid. The order of steps of the preparation method according to the present disclosure is specific. The acid treatment is conducted after the annealing treatment, which may avoid or reduce the influence of acid on inorganic piezoelectric particles.
2. Treating a ferroelectric polymer with ultrasound may allow for a higher piezoelectric activity. When the ultrasound is pulsed ultrasound, it has a better effect of improving the piezoelectric property than the continuous ultrasound and biological functions thereby produced further.
3. The present disclosure also prepares medical materials by electrospinning. It is surprisingly found that poly (L-lactic acid) composite membranes obtained by this method may settle the problems of currently available poly(L-lactic acid) about a low piezoelectric property and failure to regulate the electrical output performance leading to the limitations in bone defect repair, and thus incompatible with the complex regulatory mechanism in the bone repair process in an organism. Besides, by driving the poly(L-lactic acid) nanofiber membrane with low-intensity pulsed ultrasound and taking advantage of the adaptation of its multi-stage electrical properties and degradation properties to compatible to regulate the bone defect repair, it is possible to non-invasively regulate the electroactivity of the material in vitro and achieve on-demand power supply to meet the requirements for materials at different stages of injury repair.
4. The preparation method of the present disclosure is simple in technology, low in requirements for devices and easy to handle, easy to control the performance, and economical.

The method of adjusting the antimicrobial activity in the present disclosure has the following advantages:

Existing antimicrobial methods have problems with poor drug resistance or poor stability of antimicrobial ingredients. With the adoption of different annealing temperatures in combination with the poling process, the present disclosure kills bacteria effectively by regulating the charge amount of the ferroelectric material. Compared with non-charged, low-charged, and medium-charged ferroelectric materials, the High-charged ferroelectric materials have stronger antimicrobial effects. In addition, the antimicrobial method of the present disclosure makes the ferroelectric materials charged without applying any external force to thereby achieve the antimicrobial effect.

BRIEF DESCRIPTION OF THE DRAWINGS

FIG. 6A shows images of skin wound healing in mice within 0 to 8 days; FIG. 6B shows a quantitative statistical chart of wound diameters; and FIG. 6C shows the colony forming units of bacteria in tissues at day 3 and day 8. Among these, in each group of pictures corresponding to each day in FIG. 6B are, from left to right, the blank group (Blank), the non-charged group (NC), and the charged group (HC) successively.

FIG. 7A shows the Micro CT images and the statistical chart of bone loss of the second molars in mice at day 10 after silk ligation; and FIG. 7B shows the Micro CT images and the statistical charts of bone loss at 2 week, 3 week, and 4 week after treatment with different membrane materials.

FIG. 8A shows the HE staining images of the second molars on the palatal side of mice at 3 week and 4 week after treatment; and FIG. 8B shows a statistical bar chart of attachment loss at 3 week and 4 week after treatment, which includes, from the left to right, the blank group (Blank), non-charged group (NC), and charged group (HC) successively.

Example 1, Example 2, Example 3, and Example 4 shown in FIG. 9 to FIG. 16 correspond to Example 1B, Example 2B, Example 3B, and Example 4B of the specification of the present application, respectively.

Figure 9:
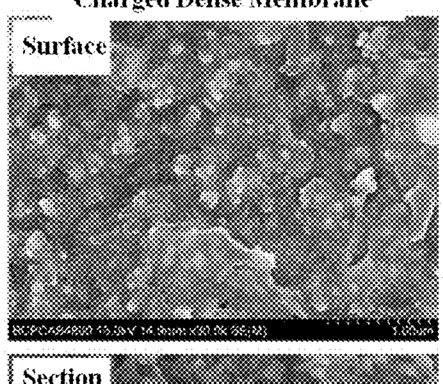
Figure 9:
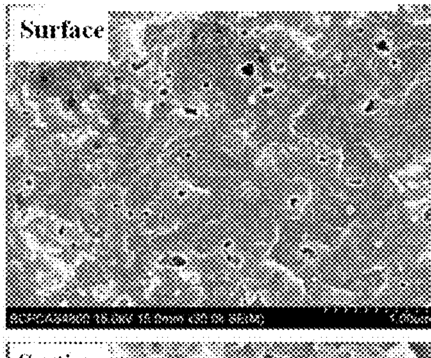
Figure 9:
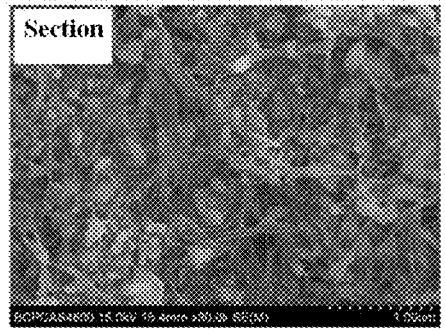
Figure 9:
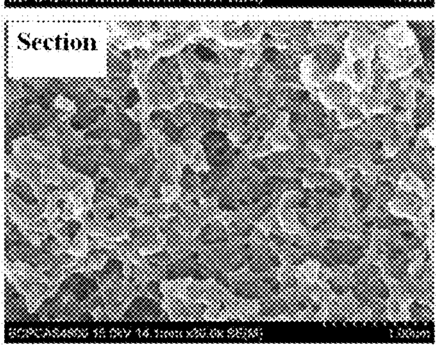

FIG. 9 shows the SEM images of the surface and section morphology of the tissue repair membrane with both breathability and high electroactivity according to Example 1B of the present disclosure. Among them, the images in the left column are for the charged dense membrane and the images in the right column are for the membrane of Example 1B. The charged dense membrane is a zinc oxide-containing membrane that has not been acid-etched.

Figure 10:
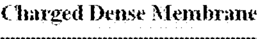
Figure 10:
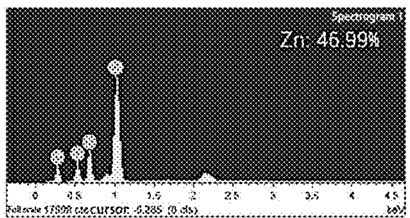
Figure 10:
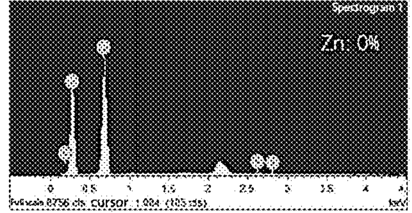

FIG. 10 shows the results of EDS analysis of the tissue repair membrane with both breathability and electroactivity in Example 1B of the present disclosure. Of these, the image in the left column is for the charged dense membrane and the image in the right column is for the membrane of Example 1B. The charged dense membrane is a zinc oxide-containing membrane that has not been acid-etched.

Figure 11:
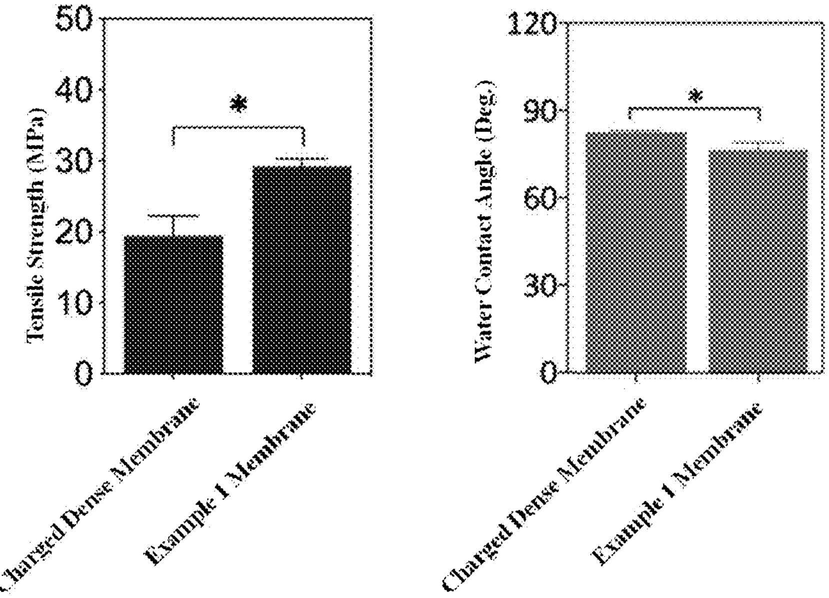

FIG. 11 shows the test results of the tensile strength (left) and water contact angle (right) of the tissue repair membrane with both breathability and electroactivity in Example 1B of the present disclosure.

Figure 12:
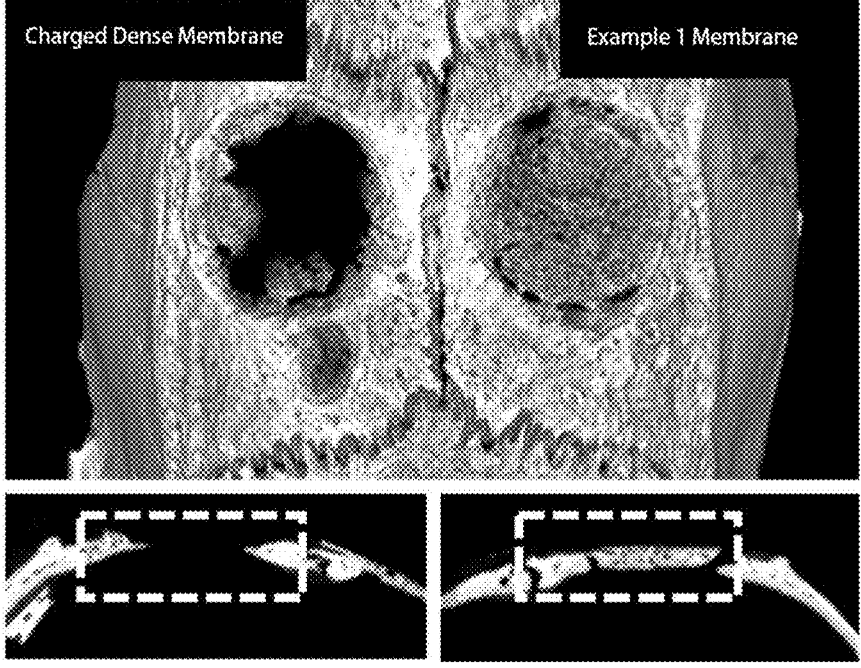

FIG. 12 shows a picture of the repair effect, detected by micro CT, of the tissue repair membrane described in Example 1B of the present disclosure after implanted into a rat skull defect for 4 weeks.

Figure 13:
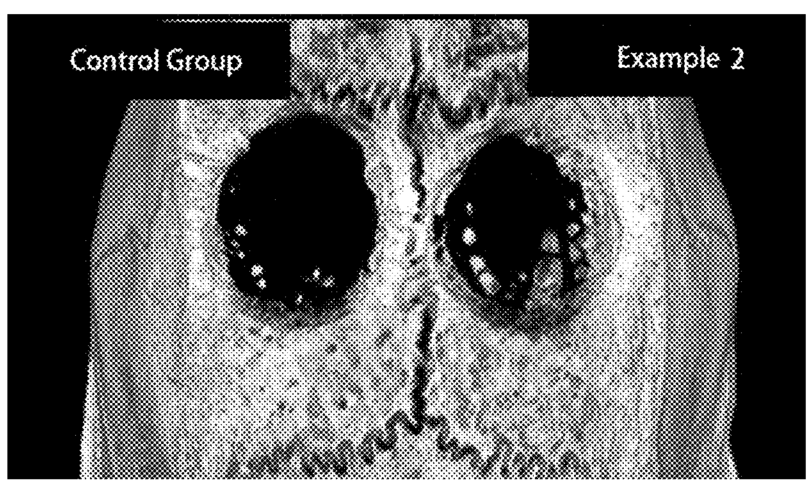

FIG. 13 shows a picture of the repair effect, detected by micro CT, of the tissue repair membrane described in Example 2B of the present disclosure after implanted into a rat skull defect for 4 weeks.

Figure 14:
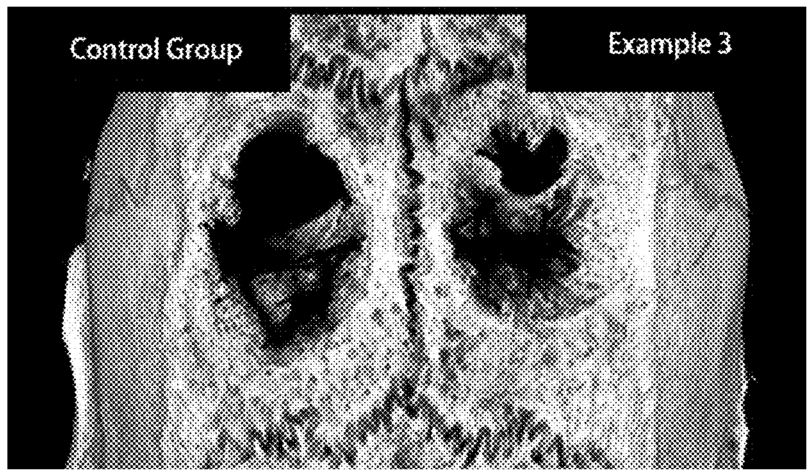

FIG. 14 shows a picture of the repair effect, detected by micro CT, of the tissue repair membrane described in Example 3B of the present disclosure after implanted into a rat skull defect for 4 weeks.

Figure 15:
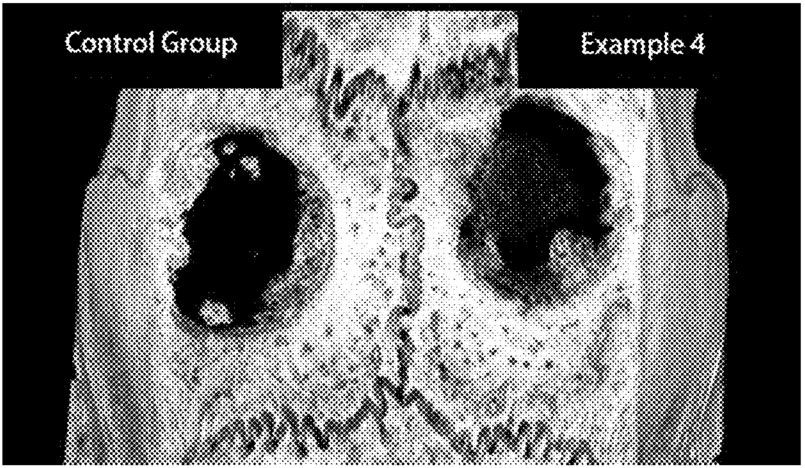

FIG. 15 shows a picture of the repair effect, detected by micro CT, of the tissue repair membrane described in Example 4B of the present disclosure after implanted into a rat skull defect for 4 weeks.

Figure 16:
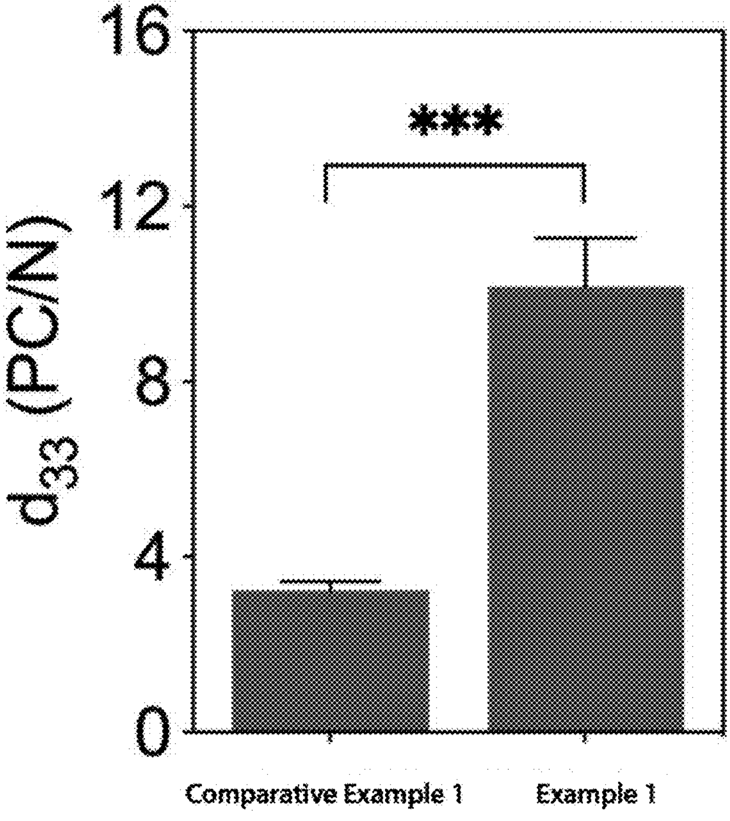

FIG. 16 shows the test results of the piezoelectric constant of the repair membrane with breathability obtained in Comparative Example 1B of the present disclosure.

Figure 17:
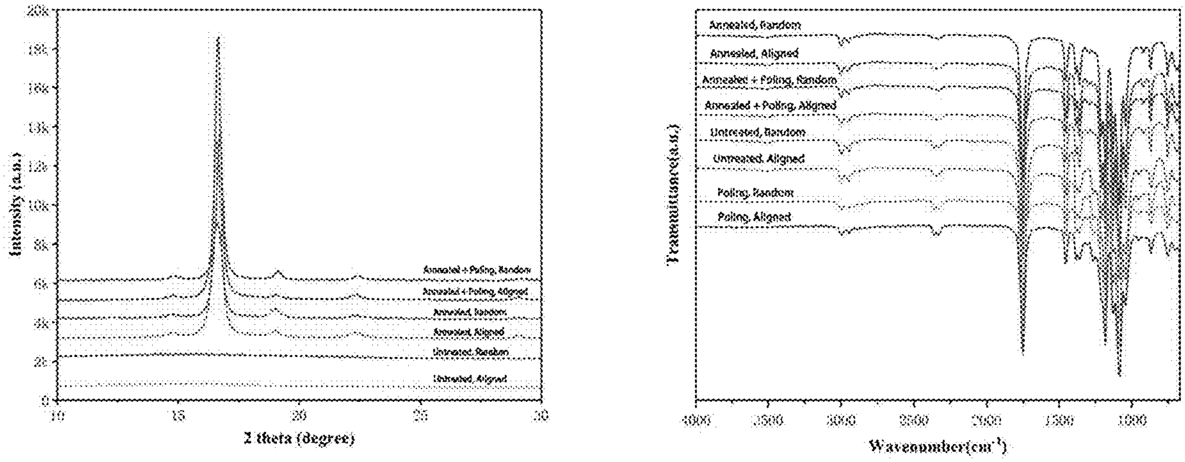

FIG. 17 shows the XRD and FTIR detection results of the poly(L-lactic acid) nanofiber membrane. In the left figure, each curve represents aligned, random, annealed aligned, annealed random, p-annealed aligned, p-annealed random in order from bottom to top. In the right figure, each curve represents annealed random, annealed aligned, p-annealed random, p-annealed aligned in order from bottom to top, p represents poling.

Figure 18:
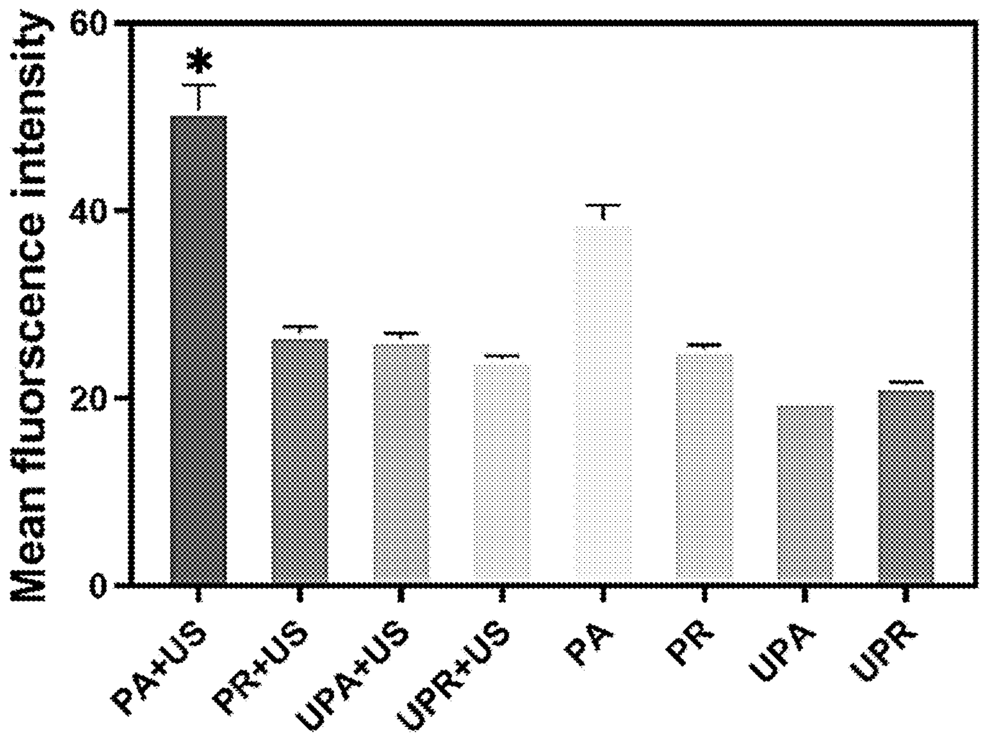

FIG. 18 shows the influence of ultrasonic treatment on the osteogenic effect.

Figure 19:
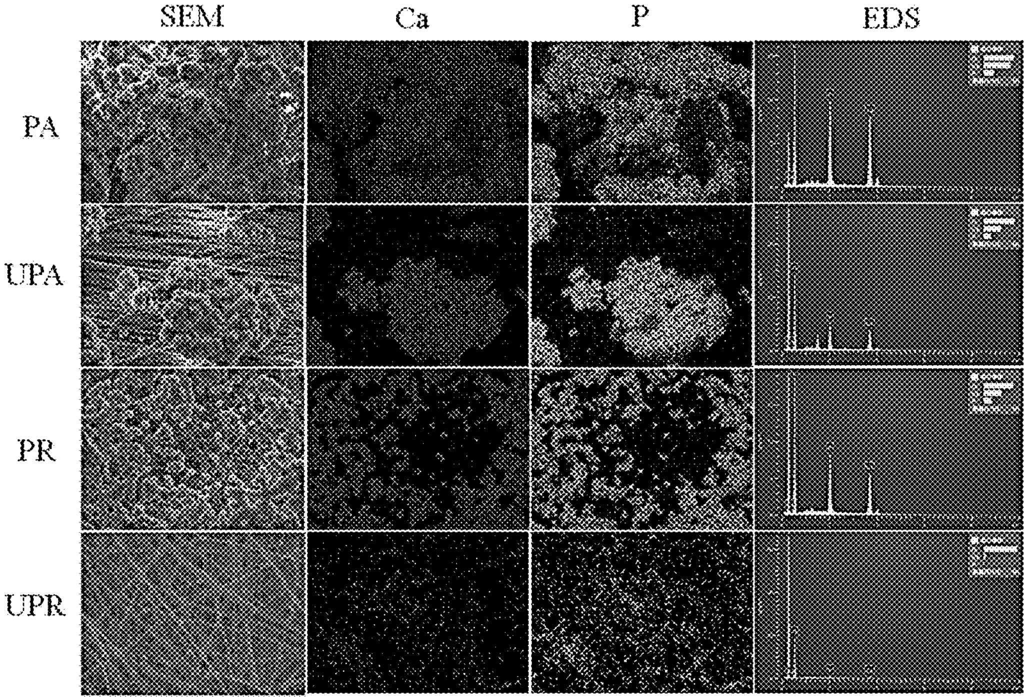

FIG. 19 shows the biomineralization effect.

DETAILED DESCRIPTION

Various exemplary embodiments of the present disclosure will be described below in detail, which shall not be construed as limitations on the present disclosure, but rather as more detailed descriptions of some aspects, features, and embodiments of the present disclosure.

It should be appreciated that the terms as used herein are only intended to describe particular embodiments, instead of limiting the present disclosure. In addition, the numerical ranges used herein shall be construed to disclose the upper limit and lower limit of this range and every intermediate value therebetween. Every smaller range between any stated value or value intermediate in the stated range and any other stated value or value intermediate in the other stated range is also included within the present disclosure. The upper limits and lower limits of these smaller ranges may independently be included in or excluded from the range.

As used herein, the term “antimicrobial” refers to an antimicrobial effect resulting from the charged property of the ferroelectric material per se, rather than resulting from a chemical component or resisting bacteria due to the electricity generated by an external force.

As used herein, the term “tissue repair membrane” refers to a polymer membrane used for tissue defect repair or as a biomedical product, especially for bone defects, such as skull defect repair. Preferably, it refers to a tissue repair membrane used to create a closed environment in the body. Compared with existing tissue repair membranes, the tissue repair membrane of the present disclosure boasts both breathability and electroactivity.

As used herein, the term “breathability” refers to a property of a gas such as oxygen passing through a membrane from one side of the membrane to the other side of the membrane. As used herein, breathability refers in particular to the ability to permeate desired gases, especially oxygen, in a closed environment that can be realized in the body. The breathability used herein is characterized by the water vapor permeance measured under the conditions of 38° C. and 90% RH.

As used herein, the term “electroactivity” means that a material has a piezoelectric activity, i.e., the property of generating micro-currents inside the material after being subjected to pressure. The bone tissue and the like in the body are natural piezoelectrics with a piezoelectric effect, which results from the collagen component of the bone. By completing the mutual conversion of mechanical energy and electrical energy, the normal physiological activities and metabolism of the bone may be maintained, which is conducive to the shaping, remodeling and functional maintenance of the bone. Poling of the bone caused by the piezoelectric effect may promote bone growth and healing. The direct piezoelectric biological effect generated in an organism is that the negatively charged surface forms a closed electric field with the defect area to promote bone formation. The electroactivity used herein refers to the ability to mimic the natural piezoelectric properties of bone tissue or the like in the body. Therefore, the “electroactivity” used herein is sometimes referred to as “biomimetic electroactivity”.

According to the first aspect of the present disclosure, there is provided a medical material, where the composite membrane is based on a ferroelectric material, the ferroelectric material comprises a ferroelectric polymer, and optionally an inorganic ferroelectric particle, and the inorganic ferroelectric particle accounts for 0 to 20% by volume of the ferroelectric polymer, and the inorganic ferroelectric particle has a diameter of from 50 nm to 500 nm.

In the present disclosure, the composite membrane is not particularly limited in form, and may be in any form, e.g., in the form of a membrane material or gel. Preferably, the medical material of the present disclosure is an antimicrobial dressing or a tissue repair membrane.

In an exemplary embodiment, the medical material of the present disclosure further comprises a porous structure in the interior.

In an exemplary embodiment, the medical material of the present disclosure further comprises a ferroelectric polymer and an inorganic ferroelectric particle.

According to the second aspect of the present disclosure, there is provided a method for preparing a medical material (e.g. a ferroelectric material-based antimicrobial dressing), comprising the following steps:

(1) preparing a composite material from a ferroelectric polymer, and optionally an inorganic ferroelectric particle (or a ferroelectric ceramic particle) and/or an inorganic pore-forming agent (used for preparing a porous antimicrobial material); and (2) subjecting the composite material to annealing treatment, corona poling treatment, and acid treatment, and optionally ultrasonic treatment, wherein the acid treatment is conducted after the annealing treatment.

In the present disclosure, it is preferred that step (1) comprises (1-1) dissolving a ferroelectric polymer into an organic solvent to form a ferroelectric polymer mixture; (1-2) adding an inorganic pore-forming agent and an inorganic ferroelectric material to the ferroelectric polymer mixture and mixing to form a dispersion; and (1-3) preparing a membrane from the dispersion by membrane casting to obtain a primary membrane.

In the present disclosure, the inorganic ferroelectric particles are not limited in size, but generally have an average diameter of from 50 nm to 500 nm, preferably from 100 nm to 400 nm, more preferably from 200 nm to 300 nm.

In the present disclosure, examples of the inorganic ferroelectric material include, but are not limited to, at least one of barium titanate, barium strontium titanate, strontium titanate, bismuth ferrite, potassium sodium niobate, and lithium niobate.

In the present disclosure, the particle size of the inorganic pore-forming agent is generally from 40 nm to 100 nm, preferably from 50 nm to 90 nm. This particle size range is conducive to uniform dispersion of the pore-forming agent in the polymer mixture. If the particle size of the inorganic pore-forming agent is too large, the antimicrobial property after poling becomes poor despite the increased breathability of the resulting membrane material. Besides, the strength of the resulting membrane material becomes low and the inorganic pore-forming particles tend to precipitate in the polymer, which is not conducive to dispersion. On the other hand, if the particle size of the inorganic pore-forming agent particles is too small, the breathability tends to deteriorate, and agglomeration easily occurs between the inorganic pore-forming agent particles when the mixed polymer solution is added, which is also unfavorable to dispersion, thus affecting the breathability and strength of the resulting membrane material.

In the present disclosure, it is desirable that the amount of the inorganic pore-forming particles is from 5% to 15% based on the weight of the dispersion. If the amount is too low, the breathability becomes poor, which cannot meet the requirement for breathability of the in vivo tissues, for example. On the other hand, if the amount is too high, the antimicrobial property after poling becomes poor or the strength of the membrane material is even affected.

In the present disclosure, the inorganic pore-forming agent particles are selected from zinc oxide and/or calcium carbonate. In the present disclosure, one of the above particles may be used or two or more of them may be used in combination.

In the present disclosure, the ferroelectric polymer is not limited, including polyvinylidene fluoride or copolymers thereof, examples of which include, but are not limited to, polyvinylidene difluoride, polyvinylidene fluoride-hexafluoropropylene, and polyvinylidene fluoride-trifluoroethylene, and polylactic acid. In the present disclosure, one of the above polymers may be used or two or more of them may be used in combination. In case of using two or more of the above polymers in combination, the amount of each of the polymers or the amount ratio among the polymers is not particularly limited and may be freely set by a person skilled in the art as actually needed. The molecular weight of the ferroelectric polymer is not limited, and is generally between 200,000 and 1,000,000 Dalton, preferably between 300,000 and 800,000 Dalton, more preferably between 400,000 and 600,000 Dalton.

In the present disclosure, the organic solvent is not particularly limited, and is preferably an aprotic polar solvent. Examples of the organic solvent include, but are not limited to, at least one of N,N-dimethylformamide, toluene, chloroform, dichloromethane, methanol, and ethyl acetate, particularly preferably include N,N-dimethylformamide. The solvent of the present disclosure may be a single solvent or a mixed solvent such as a mixed solvent of N,N-dimethylformamide and toluene or a mixed solvent of N,N-dimethylformamide and chloroform. When the solvents are mixed, the proportion of each solvent is not specific and may be any proportion so long as it does not affect the fulfillment of the objective of the present disclosure.

In the present disclosure, it is desirable that the amount ratio of the ferroelectric polymer to the organic solvent is such that the amount of the ferroelectric polymer is from 5% to 40%, preferably from 10% to 30% by weight. If the proportion of the ferroelectric polymer is too low, the charged property of the resulting repair membrane tends to decrease. On the other hand, if the proportion of the ferroelectric polymer is too high, the breathability becomes poor.

In the present disclosure, in order to facilitate mixing between the ferroelectric polymer and the organic solvent, stirring may be performed during mixing, for example. The stirring conditions are not limited, and the stirring may be carried out by any known stirring method. The stirring time is not specific either, as long as both of them are fully mixed or completely dissolved. Alternatively, in order to facilitate mixing between them, the temperature at which the ferroelectric polymer is mixed with the organic solvent may be raised, but this temperature is required to be lower than the boiling point of the organic solvent and at the same time lower than the lowest temperature for the subsequent annealing treatment, i.e. lower than 80° C., preferably lower than 70° C.

In the present disclosure, the treatment of material comprises carrying out the corona poling treatment before the acid treatment, and optionally, further carrying out the annealing treatment before the acid treatment. In the present disclosure, the acid treatment cannot be carried out before the poling treatment. In an exemplary embodiment, the order of treatment is annealing treatment, corona poling treatment, and acid treatment successively.

In the present disclosure, the acid treatment means that a material is immersed in an acidic solution and treated for 5 to 30 h, for example, 6 h, 7 h, 8 h, 10 h, 12 h, 14 h, 16 h, 18 h, or even 24 h or more.

In the present disclosure, the acidic solution is not particularly limited. Examples of the acidic solution include, but are not limited to, aqueous solutions of hydrochloric acid, sulfuric acid, nitric acid, and carbonic acid. In the present disclosure, one of the above acids may be used or two or more of them may be used in combination. In case of combination, the proportion of each of the acids is not particularly limited. The concentration of the acid in the acidic solution is not particularly limited as long as it enables the pH in the solution to be less than 7, preferably 6, more preferably 5. In general, the mass percent concentration of the acid in the aqueous solution is 5% to 60%, preferably 6% to 50%, more preferably 10% to 40%. The time of treatment with the acidic solution is not limited and is generally 5 h or more, for example, 10 h, 12 h, 15 h, 20 h, 25 h, or 30 h. By treating with an acidic solution, the breathability of the membrane material is increased. The acid concentration and treatment time are generally related to the content of the inorganic pore-forming agent particles, the concentration of the polymer, etc.

In the present disclosure, the annealing treatment is generally to treat the antimicrobial material at 80° C. to 100° C. for 5 to 30 min. The annealing temperature may be, e.g. 85° C., 90° C., 95° C., and 100° C. If the temperature is too low, the effect of reducing the adverse effects on corona poling tends to be weakened or even fails. If the temperature is too high, the breathability of the membrane material tends to become poor, or the requirement for oxygen exchange in the in vivo tissues cannot even be met.

In the present disclosure, the parameters for the corona poling treatment include: the polarization medium is either of air and methyl silicone oil, and the polarization voltage is 1 kV to 30 kV, more preferably 2 kV to 25 kV. The distance between the electrode tip and the sample is set to 1 mm to 50 mm, e.g. 5 mm, 10 mm, 15 mm, 20 mm, 25 mm, 30 mm, and 35 mm. The polarization temperature is from 20° C. to 50° C., e.g. 25° C., 30° C., 35° C. or 40° C. The polarization time is from 1 min to 60 min, e.g. 5 min, 10 min, 15 min, 20 min, 30 min, or 40 min.

According to the third aspect of the present disclosure, there is provided a method for preparing a medical material, wherein the method comprises the following steps:

(1) dissolving a ferroelectric polymer into an organic solvent to form a ferroelectric polymer mixture;

(2) adding at least one inorganic particle selected from zinc oxide, calcium carbonate, and barium titanate to the ferroelectric polymer mixture and mixing to form a dispersion;

(3) preparing a membrane from the dispersion by membrane casting to obtain a primary membrane, and immersing the primary membrane into an acidic solution for treatment to obtain a breathable polymer membrane; and (4) subjecting the breathable polymer membrane to the annealing treatment at 80° C. to 100° C. for 5 to 30 min, then to natural cooling at room temperature, and subsequently to the corona poling treatment, thereby obtaining a composite membrane (e.g. a tissue repair membrane) with both breathability and electroactivity.

A person skilled in the art shall be appreciated that numberings such as (1) and (2) are only for the purpose of differentiating different steps and do not indicate the order of the steps. As long as the objective of the present disclosure can be fulfilled, the order of the above steps is not particularly limited. In addition, two or more of the above steps may be combined and carried out concurrently. For instance, steps (1) and (2) may be carried out concurrently, that is, two steps may be separately carried out at the same time, or steps (1) and (2) may be combined and carried out as a single step. Under this circumstance, the ferroelectric polymer and inorganic particle may be simultaneously mixed in an organic solvent, for example. Furthermore, a person skilled in the art shall also be appreciated that other steps or operations may be further included before or after steps (1) to (4) described above or between any two of these steps to, for example, further optimize and/or improve the method according to the present disclosure. Each of the steps will be described in detail below.

Step (1)

In the present disclosure, step (1) is a step of preparing a polymer mixture or solution, comprising dissolving a ferroelectric polymer into an organic solvent. The ferroelectric polymer, organic solvent, amount ratio therebetween, and mixing method and conditions employed in this step are the same as those described in the second aspect of the present disclosure.

Step (2)

In the present disclosure, step (2) is a step of mixing an inorganic particle, comprising a step of adding an inorganic particle to the ferroelectric polymer mixture and mixing to form a dispersion. The inorganic particle is a particle used for improving the breathability of the membrane. The particle size of the inorganic particle is generally from 40 nm to 100 nm, preferably from 50 nm to 90 nm. This particle size range is conducive to uniform dispersion of the inorganic particles in the polymer mixture. If the particle size of the inorganic particle is too large, the charged property after poling becomes poor despite the increased breathability of the resulting repair membrane. Besides, the strength of the repair membrane becomes low and the inorganic particles tend to precipitate in the polymer mixture, which is not conducive to dispersion. On the other hand, if the particle size of the inorganic particle is too small, the breathability tends to deteriorate, and agglomeration easily occurs between the inorganic particles when a polymer mixture is added, which is also unfavorable to dispersion, thus affecting the breathability and strength of the resulting repair membrane.

In the present disclosure, it is desirable that the amount of the inorganic particles is from 5% to 15% based on the weight of the dispersion obtained in step (2). If the amount is too low, the breathability becomes poor, which cannot meet the requirement for breathability of the in vivo tissues in the closed area. On the other hand, if the amount is too high, the charged property after poling becomes poor or the strength of the repair membrane is even affected.

In the present disclosure, the inorganic particle is selected from zinc oxide, calcium carbonate, and barium titanate. In the present disclosure, one of the above particles may be used or two or more of them may be used in combination. For example, a combination of barium titanate with zinc oxide, a combination of barium titanate with calcium carbonate, or a combination of barium titanate with zinc oxide and calcium carbonate may be used.

In case of combination, the amount ratio of each of the particles is not particularly limited, and may be any desired ratio.

In the present disclosure, in order to facilitate mixing or dispersion of the inorganic particles in the polymer mixture, stirring may be performed during mixing, for example. The stirring conditions are not limited, and the stirring may be carried out by any known stirring method. The stirring time is not specific either, as long as both of them are fully mixed or completely dissolved. Preferably, shaking treatment is further adopted to facilitate dispersion of the inorganic particles. For example, treatment with ultrasonic shaking is carried out for a specified time, e.g. 10 min to 3 h, to facilitate uniform dispersion.

Step (3)

Step (3) in the present disclosure is a step of preparing a breathable polymer membrane, comprising preparing a membrane from the dispersion obtained in step (2) by membrane casting to obtain a primary membrane, and immersing the primary membrane into an acidic solution for treatment to obtain a breathable polymer membrane.

In the present disclosure, the membrane casting comprises coating the dispersion on at least part of the surface of the substrate. The substrate is generally in a shape of a flat plate, and the material thereof is not limited, examples of which include, but are not limited to, glass, stainless steel, plastics and/or ceramics. The membrane casting further comprises scraping the membrane with a scraper to control the flatness and/or thickness of the membrane.

The acidic solution used in the present disclosure is the same as that described in the second aspect of the present disclosure. By treating with an acidic solution, the breathability of the tissue repair membrane is improved. The acid concentration and treatment time are generally related to the content of the inorganic particles, the concentration of the polymer, etc.

Step (4)

In the present disclosure, step (4) is a step of subjecting to annealing treatment and corona poling treatment, comprising subjecting the breathable polymer membrane to the annealing treatment at 80° C. to 100° C. for 5 to 30 min, then to natural cooling at room temperature, and subsequently to the corona poling treatment, thereby obtaining a tissue repair membrane with both breathability and electroactivity.

In the present disclosure, the annealing treatment is used to reduce the adverse effects on corona poling caused by the acidic solution treatment, and improve the charged property of the membrane material after poling. The annealing treatment is generally to treat the breathable polymer membrane at 80° C. to 100° C. for 5 to 30 min. The annealing temperature may be, e.g. 85° C., 90° C., 95° C., and 100° C. If the temperature is too low, the effect of reducing the adverse effects on corona poling tends to be weakened or even fails. If the temperature is too high, the breathability of the membrane material tends to become poor, or the requirement for exchange of, e.g. oxygen in the in vivo closed area cannot even be met.

In the present disclosure, the conditions of the corona poling treatment are the same as those described in the second aspect of the present disclosure.

Optional Steps

In addition to steps (1) to (4) described above, the preparation method according to the present disclosure may further comprise other optional steps. Exemplarily, a step of optionally treating the substrate may be further included between step (2) and step (3). Exemplarily, a step of optionally drying the cast membrane may be further included between step (3) and step (4).

In the present disclosure, the step of treating the substrate comprises wiping or washing the substrate material. In the present disclosure, a wiping reagent is preferably anhydrous ethanol, and the specific process of wiping is as follows: wiping with a piece of lens wiping paper dipped in anhydrous ethanol. Washing preferably comprises washing with acetone, washing with first deionized water, washing with anhydrous ethanol, and washing with second deionized water, successively. In the present disclosure, washing with first deionized water, washing with anhydrous ethanol, and washing with second deionized water are preferred. The present disclosure does not limit the specific amounts of the washing reagents used in the above washing process.

In the present disclosure, the drying step comprises drying the scraped membrane, which is formed by dumping the membrane casting solution of the polymer on the substrate, at 30° C. to 75° C. for 10 min to 24 h, preferably 30 min to 20 h, more preferably 1 h to 10 h, e.g. 2 h, 4 h, 6 h, or 8 h. If the drying temperature is too high or the drying time is too long, the breathability of the resulting membrane material will be affected. If the drying temperature is too low or the drying time is too short, the solvent cannot be favorably removed, which affects the properties of the membrane material.

According to the fourth aspect of the present disclosure, there is provided a method for preparing a medical material, wherein the method comprises the following steps:

(1) dissolving a ferroelectric polymer into an organic solvent, and optionally adding an inorganic ferroelectric particle and/or an inorganic pore-forming agent to form a ferroelectric polymer mixture;

(2) transferring the ferroelectric polymer mixture to an electrospinning syringe for electrospinning; and (3) subjecting a membrane formed after completion of spinning to drying at room temperature and then to at least one of annealing treatment, corona poling treatment, acid treatment, and ultrasonic treatment.

In the present disclosure, the above method may comprise the following specific operations, which will be illustrated with poly(L-lactic acid) as a ferroelectric polymer:

Spinning Process 0.49 g of ferroelectric polymer (e.g. poly(L-lactic acid)) powder is weighed and added to 7 ml of trifluoroethanol, and stirred magnetically for 3 h until the powder is completely dissolved to a clear and uniform solution. 7 ml of the mixed solution is transferred into an electrospinning syringe with a 22 G special needle. The outlet of the needle and the roller receiver covered with an aluminum foil are connected to the high-voltage power supply of the spinning machine, respectively. The electrospinning equipment is turned on, and the positive voltage is adjusted to 10.57 kV, the negative voltage to 3.05 kV, the injection rate to 0.065 mm/min, the rotation speed of the roller receiver to 300 to 2800 rpm, and the distance from the needle to the roller receiver to 12 cm. The spinning is completed 8 h later.

Annealing Treatment

A membrane with an aluminum foil is put in an oven and dried at room temperature for 24 h, and then put in a heating platform. A first-step annealing temperature is set to 105° C. for 10 h. When the temperature drops to room temperature, the membrane is taken out and peeled off from the aluminum foil. The membrane is put in the heating platform again. A second-step annealing temperature is set to 160° C. for 10 h. In the annealing process, the membrane is clamped with a heat-resistant quartz glass plate to prevent shrinkage. When the temperature drops to room temperature, the membrane is taken out.

Poling Treatment

The annealed membrane is subjected to the corona poling treatment. The parameters include: polarization voltage 16 kV, polarization distance 15 mm, polarization temperature 25° C., and polarization time 30 min.

Ultrasound Loading

Low-intensity pulsed ultrasound is loaded with the parameters of operating frequency 1 MHz and effective sound intensity 1 W/cm$^2$ in a manner of output pulse.

The above treated poly(L-lactic acid) nanofiber membrane is tested for the piezoelectric coefficient and output voltage to test its effects of promoting osteogenesis of rBMSCs and healing in bone defects.

EXAMPLES

(I) Preparation of Antimicrobial Dressing, Method for Regulating Antimicrobial Activity, and Performance Detection of Antimicrobial Dressing

Example 1A

The present example was a preparative example of an exemplary antimicrobial dressing, which specifically involved the following steps:

(1) Barium titanate nanoparticles were put into an aqueous dopamine solution, heated and stirred in a water bath at 60° C. for 12 h, centrifuged and dried to obtain a barium titanate nanoparticle filler.

(2) An appropriate amount of the barium titanate nanoparticle filler prepared in step (1) was weighed and dispersed in 3 ml of an organic solvent DMF, and stirred for 3 h by stirring in conjunction with ultrasonic shaking to obtain a dispersion of the barium titanate particle filler.

(3) 1 g of polymer P(VDF-TrFE) powder was weighed and dispersed in 7 ml of an organic solvent DMF, and stirred for 3 h to make it completely dissolved to form a polymer P(VDF-TrFE) solution.

(4) The dispersion of the barium titanate particle filler formed in step (2) and the polymer P(VDF-TrFE) solution formed in step (3) were mixed and then stirred for 24 h to obtain a mixed solution in which the particle filler was homogenously dispersed.

(5) The mixed solution obtained in step (4) was weighed separately and cast in a casting container to form membranes, dried at 55° C. for 4 h, so as to completely volatilize the solvent.

Figure 1:
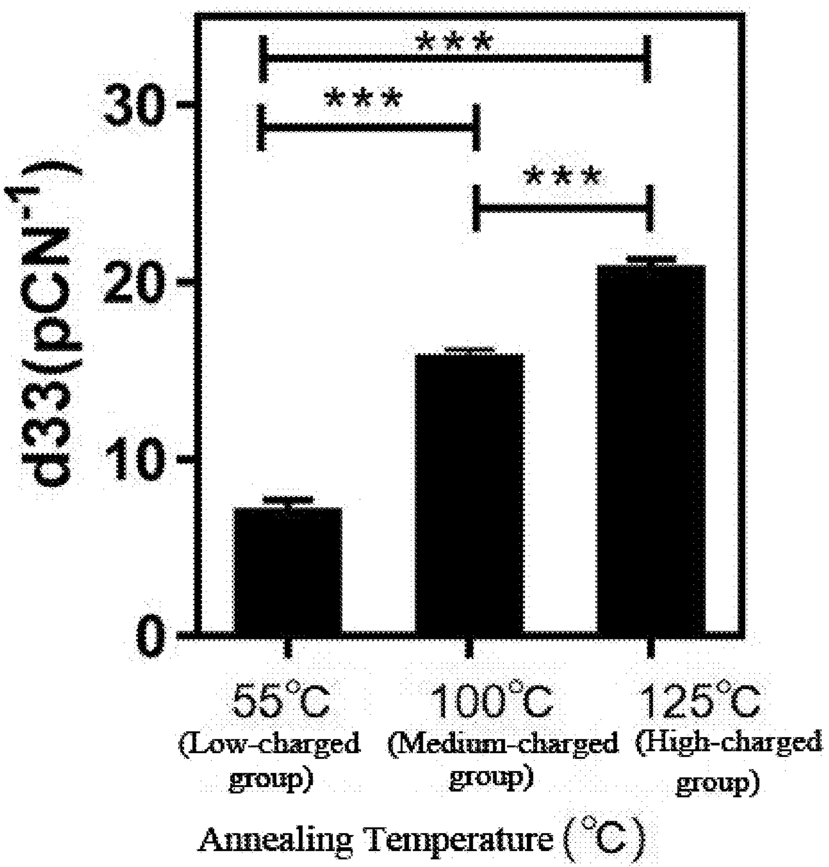
FIG. 1 shows the characterization results of different charge amounts (piezoelectric constant $d_{33}$) of different materials prepared in Example 1A of the present disclosure.

(6) The composite membrane prepared in step (5) was placed on a heating platform and annealed for 30 min under the conditions of 100° C. and 125° C. A total of two kinds of ferroelectric composite membranes treated at different temperatures were obtained together with the composite membrane that was not annealed in step (5). They were then placed on the sample stage of a corona poling device respectively, where the polarization medium was air, the applied voltage was 21 kV, the distance from the polarization electrode tip to the sample was set to 15 mm, the polarization temperature to 25° C., and the poling was carried out for 30 min to obtain three $BaTiO_3$/P(VDF-TrFE) antimicrobial composite membrane materials with different charge amounts, which had piezoelectric constant $d_{33}$ of 8 pC/N, 15 pC/N, and 21 pC/N (as shown in FIG. 1), respectively. The water vapor permeance was measured as about 54 $g/m^2 \cdot 24$ h.

Example 2A to Example 4A

Antimicrobial membrane materials were prepared by the same method of Example 1A except for changing the material composition or treatment method as shown in Table 1A.

TABLE 1A

| | Example 2A | Example 3A | Example 4A |
|---|---|---|---|
| Ferroelectric material | Strontium titanate | Potassium sodium niobate | Lithium niobate |
| Annealing treatment | 100° C., 30 min | 90° C., 30 min | None |
| Piezoelectric constant (pc/V) | 15 | 13 | 8 |

Example 5A

The present example was an exemplary preparative example of a porous antimicrobial dressing. When preparing porous antimicrobial dressings using an inorganic pore-forming agent, the present inventors discovered that acid treatment would corrode the ferroelectric inorganic particles in the composite membrane, and different ferroelectric materials had different resistance to the acidic solution, where barium titanate BTO was least influenced, while potassium sodium niobate KNN and barium strontium titanate BST were greatly influenced during the acid treatment. Besides, the present inventors further discovered that corrosion of the ferroelectric materials exerted an influence on the improvement of the piezoelectric constant when poling the composite materials, thereby affecting the antimicrobial property.

TABLE 2A

| | | KNN | BTO | BST | ZnO | $CaCO_3$ |
|---|---|---|---|---|---|---|
| Dissolution rate in acid treatment (%) | 12 h | 27.28 | 6.74 | 82.41 | 100 | 100 |
| | 24 h | 33.29 | 7.02 | 90.33 | 100 | 100 |

To avoid the above-mentioned influences, the present inventors improved the preparation process for porous antimicrobial dressings as follows:

(1) Ferroelectric material nanoparticles listed in Table 2A were put into an aqueous dopamine solution, heated and stirred in a water bath at 60° C. for 12 h, centrifuged and dried to obtain a nanoparticle filler.

(2) An appropriate amount of the nanoparticle filler prepared in step (1) and 10 wt % of the inorganic pore-forming agent (having an average particle size of 80 nm) listed in Table 2A were weighed and dispersed in 3 ml of an organic solvent DMF, and stirred for 3 h by stirring in conjunction with ultrasonic shaking to obtain a dispersion.

(3) 1 g of polymer P(VDF-TrFE) powder was weighed and dispersed in 7 ml of an organic solvent DMF, and stirred for 3 h to make it completely dissolved to form a polymer P(VDF-TrFE) solution.

(4) The dispersion formed in step (2) and the polymer P(VDF-TrFE) solution formed in step (3) were mixed and then stirred for 24 h to obtain a mixed solution in which the particle filler was homogenously dispersed.

(5) The mixed solution obtained in step (4) was weighed separately and cast in a casting container to form membranes, dried at 55° C. for 4 h, so as to completely volatilize the solvent.

(6) The composite membrane prepared in step (5) was placed on a heating platform and annealed at 125° C. for 30 min, and thereafter placed on the sample stage of a corona poling device, where the polarization medium was air, the applied voltage was 21 kV, the distance from the polarization electrode tip to the sample was set to 15 mm, the polarization temperature was 25° C., and the poling was carried out for 30 min to obtain an antimicrobial composite membrane material, which was then immersed in a 37% hydrochloric acidic solution for 12 h (24 h in the experiment of regulating the antibacterial activity).

(7) The membrane prepared in step (6) was removed, washed several times with deionized water, and taken out and purged at 37° C. for 3 h to obtain the porous antimicrobial dressing.

Comparative Example 1A (1) Ferroelectric material nanoparticles were put into an aqueous dopamine solution, heated and stirred in a water bath at 60° C. for 12 h, centrifuged and dried to obtain a nanoparticle filler.

(2) An appropriate amount of the nanoparticle filler prepared in step (1) and 10 wt % of inorganic particle ZnO (having an average particle size of 80 nm) were weighed and dispersed in 3 ml of an organic solvent DMF, and stirred for 3 h by stirring in conjunction with ultrasonic shaking to obtain a dispersion.

(3) 1 g of polymer P(VDF-TrFE) powder was weighed and dispersed in 7 ml of an organic solvent DMF, and stirred for 3 h to make it completely dissolved to form a polymer P(VDF-TrFE) solution.

(4) The dispersion formed in step (2) and the polymer P(VDF-TrFE) solution formed in step (3) were mixed and then stirred for 24 h to obtain a mixed solution in which the particle filler was homogenously dispersed.

(5) The mixed solution obtained in step (4) was weighed separately and cast in a casting container to form membranes, dried at 55° C. for 4 h, so as to completely volatilize the solvent.

(6) The composite membrane prepared in step (5) was immersed in a 37% hydrochloric acidic solution for 12 h (24 h in the experiment of regulating the antibacterial activity). The composite membrane was removed and then washed several times with deionized water, and then taken out and purged at 37° C. for 3 h.

(7) The material in step (6) was placed on a heating platform and annealed at 125° C. for 30 min, and thereafter placed on the sample stage of a corona poling device, where the polarization medium was air, the applied voltage was 21 kV, the distance from the polarization electrode tip to the sample was set to 15 mm, the polarization temperature was 25° C., and the poling was carried out for 30 min to obtain an antimicrobial composite membrane material.

Comparative Example 2A (1) Ferroelectric material nanoparticles were put into an aqueous dopamine solution, heated and stirred in a water bath at 60° C. for 12 h, centrifuged and dried to obtain a nanoparticle filler.

(2) An appropriate amount of the nanoparticle filler prepared in step (1) and 10 wt % of inorganic particle ZnO (having an average particle size of 80 nm) were weighed and dispersed in 3 ml of an organic solvent DMF, and stirred for 3 h by stirring in conjunction with ultrasonic shaking to obtain a dispersion.

(3) 1 g of polymer P(VDF-TrFE) powder was weighed and dispersed in 7 ml of an organic solvent DMF, and stirred for 3 h to make it completely dissolved to form a polymer P(VDF-TrFE) solution.

(4) The dispersion formed in step (2) and the polymer P(VDF-TrFE) solution formed in step (3) were mixed and then stirred for 24 h to obtain a mixed solution in which the particle filler was homogenously dispersed.

(5) The mixed solution obtained in step (4) was weighed separately and cast in a casting container to form membranes, dried at 55° C. for 4 h, so as to completely volatilize the solvent.

(6) The composite membrane prepared in step (5) was immersed in a 37% hydrochloric acidic solution for 12 h (24 h in the experiment of regulating the antibacterial activity). The composite membrane was removed and then washed several times with deionized water, and taken out and purged at 37° C. for 3 h.

(7) The material in step (6) was placed on the sample stage of a corona poling device, where the polarization medium was air, the applied voltage was 21 kV, the distance from the polarization electrode tip to the sample was set to 15 mm, the polarization temperature was 25° C., and the poling was carried out for 30 min to obtain an antimicrobial composite membrane material.

Test Examples

1. Antibacterial Experiment

Figure 2:
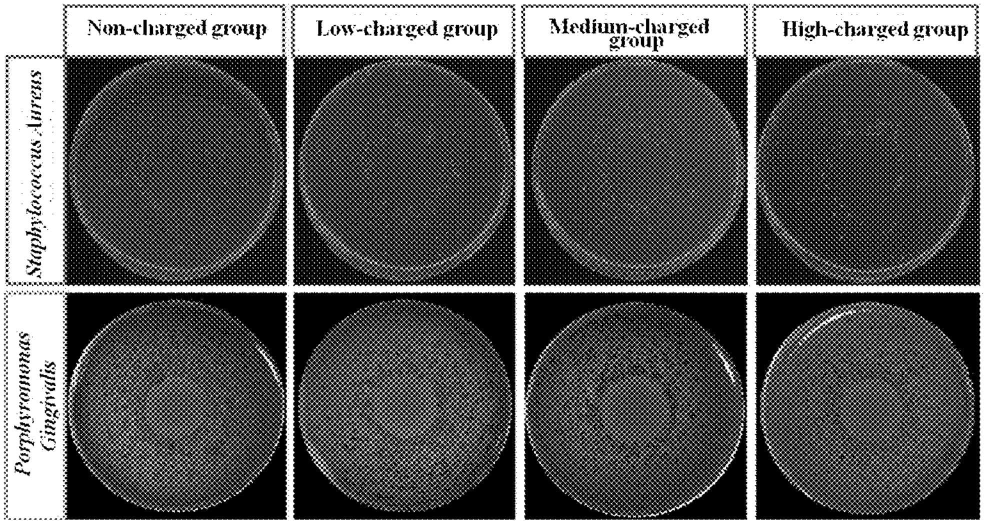
FIG. 2 shows photos of *Staphylococcus aureus* and *Porphyromonas gingivalis* colonies cultured on the surfaces of materials with different charge amounts in Example 1A of the present disclosure.
Figure 3:
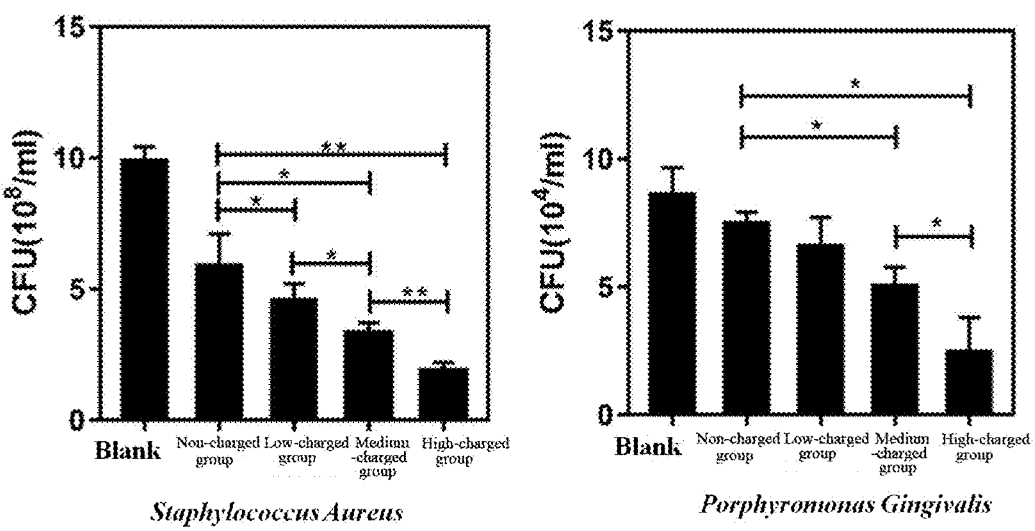
FIG. 3 shows the analysis results of the colony forming units (CFU/ml) of *Staphylococcus aureus* bacteria and the colony forming units (CFU/ml) of *Porphyromonas gingivalis* bacteria cultured on the surfaces of materials with different charge amounts in Example 1A of the present disclosure.
Figure 4:
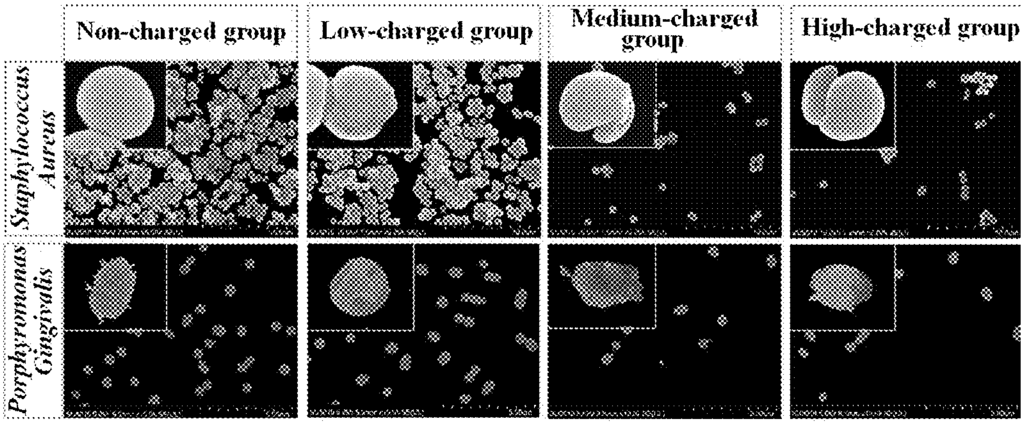
FIG. 4 shows photos of the structural morphology of *Staphylococcus aureus* bacteria and *Porphyromonas gingivalis* bacteria cultured on the surfaces of materials with different charge amounts in Example 1A of the present disclosure.
Figure 5:
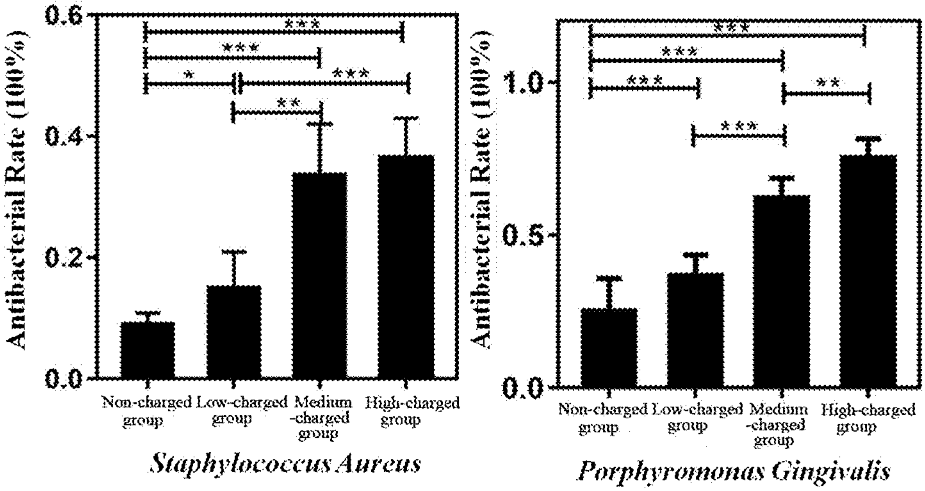
FIG. 5 shows the results of the antibacterial rates of *Staphylococcus aureus* and *Porphyromonas gingivalis* bacteria on the surfaces of materials with different charge amounts in Example 1A of the present disclosure.

The ferroelectric composite membranes with different charge amounts as obtained above were co-cultured with bacteria (Gram-negative bacteria *Porphyromonas gingivalis* and Gram-positive bacteria *Staphylococcus aureus*). 24 h later, the growth activity and structural change of the bacteria were detected, and the antibacterial rate was analyzed. An unpolarized, non-charged composite membrane served as a control group. The detection results of the present example were shown in FIG. 2, FIG. 4, and FIG. 5. The experimental results showed that the antibacterial activity was closely related to the charge amount. Compared to the non-charged group, the charged group exhibited a significant antibacterial activity, and the antibacterial activity enhanced with the increase of the charge amount, which confirmed that by regulating the charge amount, an efficient antibacterial effect could be achieved.

2. Experiment on Skin Defect Infection 2.1 Model Construction

Mice were acclimatized for 7 days. The mice were anesthetized with 1% pentobarbital at an injection dose of 50 mg/Kg. After the mice were shaved, a round full-thickness skin wound (φ8 mm) was created on the back of each mouse. Thereafter, 20 μL of *Staphylococcus aureus* solution ($10^7$ CFU/mL) were applied evenly to the wound area by two separate times, and covered with an airtight plastic membrane for fixation. 24 h later, whether the model was successfully constructed was observed (sign of success: suppuration was observed at the wound). After the model was successfully constructed, the BTO/P(VDF-TrFE) composite membrane was added to the wound for treatment and fixed by a hollow Tegaderm breathable dressing patch and a 3M adhesive. The control conditions in the blank group were the same as those in the experimental group except that materials were not used. Changes in daily body weight and wound diameters of the mice were recorded daily. The wound size (%) was calculated by the following formula: wound size=wound area on a given day/wound area on day 0×100%. The results were statistically analyzed. The mice were executed on 3 d and 8 d, respectively. Half of the tissues were homogenized and diluted to an appropriate proportion with PBS, spread on plates, and photographed for recording; and half of the tissues were immobilized with paraformaldehyde and subjected to the HE staining and Masson staining to observe pathological changes of tissues. Expression of IL-6, CD31, and KRT5 in the tissues was detected by immunohistofluorescence.

2.2 Data Analysis

All results were statistically analyzed using the SPSS17.0 software. The statistical method was analysis of variance (ANOVA). The result was represented by mean±standard deviation. $P<0.05$ indicated that there was a significant difference, * indicated $P<0.05$,  indicated $P<0.01$, and * indicated $P<0.001$.

2.3 Experimental Results

Figures 6A, 6B, 6C, 7A, 7B:
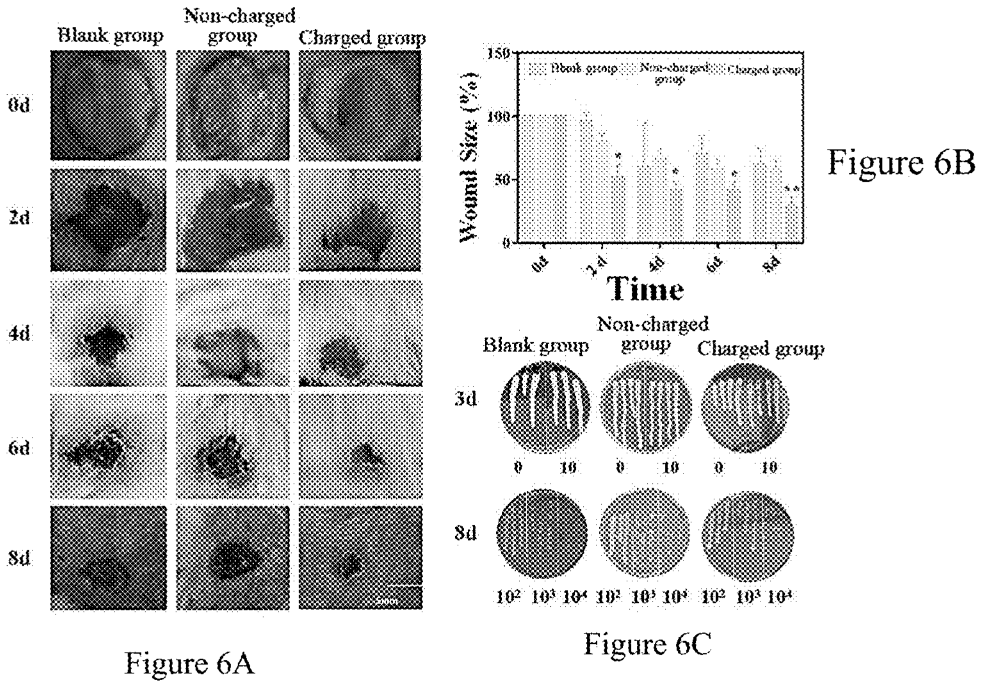
FIGS. 6A-6C show changes in skin wound healing in mice.
FIGS. 7A and 7B show the Micro CT results of mice periodontitis models.

The wound conditions of the mice were as shown in FIGS. 6A-6C. At day 0, suppuration of the wounds in mice and redness around the wounds could be observed, suggesting that *Staphylococcus aureus* bacteria successfully infected the wounds in mice and the skin defect infection model was successfully constructed. At 0 d to 8 d, it could be seen from FIG. 6A that the wound healing speed of the mice treated with the High-charged dressing (HC) obtained in Example 1 was significantly faster than that in the blank group and non-charged group (NC). The wound diameters within 8 days were statistically analyzed. The results showed that following day 2, the wound in the High-charged group of Example 1 was significantly reduced, whereas the wound healing in the blank group and non-charged group was not significant; and at day 8, the wound in mice in the High-charged group of Example 1 was substantially replaced with renascent skin, whereas the non-charged group and the blank group suggested that the charged surface could promote healing of infected skin wounds in mice FIG. 6B. At day 3 and day 8 after treatment, half of the tissues were measured, diluted, and spread on plates to verify the antibacterial effect of the charged membrane. The results were as shown in FIG. 6C. At both day 3 and day 8, the results showed that the colony forming units of the bacteria in the tissues in the High-charged group were significantly reduced as compared to the non-charged group and blank group, suggesting that the charged surface could promote healing in infected mice skin wound by inhibiting growth of bacteria.

Three labels IL-6, KRT5, and CD31 were used to evaluate the healing conditions of the mice skin wounds. Immunofluorescence results showed that at day 3 and day 8, the expression of IL-6 in the High-charged group was much lower than that in the non-charged group and the blank group and showed a decreasing trend all the time, suggesting that the charged membrane inhibited the inflammation of infected wounds in mice. Besides, the expression of the keratin KRT5 in the High-charged group increased significantly at day 3, suggesting that in the High-charged group, the proliferation and differentiation of epithelial cells were accelerated and the healing in skin wounds was promoted. Although the expression of KRT5 at day 8 was lowered, the overall level was still higher than those in the non-charged group and blank group, and was in line with the trend reported in the literature. In the High-charged group, CD31 also exhibited a higher activity at day 3 after treatment, and there were no significant differences among these several groups at day 8, suggesting that neovascularization was promoted at the early stage of repair in the High-charged group, which also indicated better wound healing in the High-charged group.

3. Experiment on Periodontitis Model 3.1 Construction of Periodontitis Model:

After mice were anesthetized with 1% pentobarbital, a silk thread (5-0) was used to ligate and tie a knot around the neck of the maxillary second molar of each mouse. The mice were injected with a suspension of *P. gingivalis* bacteria at a concentration of $10^9$ CFU/ml into the ligated molar every day. Ten days after ligation, the periodontal pocket was established. In order to ensure the uniformity and standardization of the defect, the same operator was required to perform the same step in both directions each time to overcome the operator's bias. After induction of periodontitis, jawbone destruction in mice was evaluated by micro-CT to ensure successful construction of the periodontitis model prior to the treatment.

After the periodontitis model was confirmed to be successfully constructed, the ligature was removed. The mice were randomly divided into three groups and treated for different periods of time, namely, 2 weeks, 3 weeks, and 4 weeks. The palatal gingival flap was turned over from the gingival sulci on both sides of the neck at the palatal part of the maxillary second molar by using the tips of micro-forceps, and the flap was elevated to allow the material to be placed into the palatal side of the maxillary second molar. Finally, the palatal gingiva was sutured with a microscopic suture needle with 7-0 thread to make it suspended over the tooth for fixation, and the suture was removed one week later. The left and right sides of each mouse were used as each other's control, with a charged membrane used on one side and a non-charged membrane on the other side. The other operations were the same in the blank group except that no membrane was used. At 2 week, 3 week, and 4 week after treatment, the mice were euthanized by intraperitoneal injection of pentobarbital (100 mg/kg). The maxillae of the mice were removed and fixed with 4% paraformaldehyde.

3.2 Experimental Results

The Micro CT results were as shown in FIGS. 7A and 7B. Picture FIG. 7A showed the Micro CT scanning images and the statistical chart of bone loss of mice periodontitis models at day 10 after treatment in the silk ligation group (Treat) and the control group (Control). Under normal healthy periodontal state, the distance from the cemento-enamel junction to the alveolar ridge crest was no more than 2 mm. If the distance was 2 mm or more, the bone loss would be considered to occur. Here the bone loss was calculated by the method of measuring and averaging the distances from the cemento-enamel junction to the alveolar ridge crest on the buccal and palatal side of ligated tooth. At least 6 points were measured for each tooth. Each point was repeatedly measured three times and the values were averaged, which was taken as Distance of CEJ-ABC (mm), abbreviated as Distance (mm). The greater the distance, the more the bone lost and the more significant the bone resorption was. As was clear from FIGS. 7A and 7B, the bone loss on the buccal and palatal side was significant in the ligation group, indicating that the periodontitis model was successfully constructed. Picture FIG. 7B showed that at 2 week and 3 week, there was no significant difference in the bone loss among the three groups, and at 4 week, there was still a small amount of bone loss in the non-charged group and blank group, and the bone resorption decreased or there was even a small amount of new bone in the High-charged group.

Figure 8A:
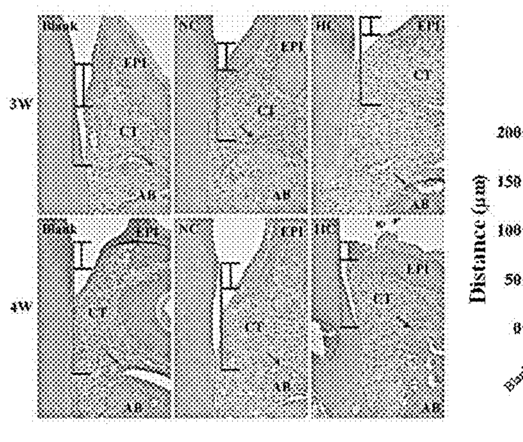
FIGS. 8A and 8B show the periodontal HE staining results of mice in Example 1A.
Figure 8B:
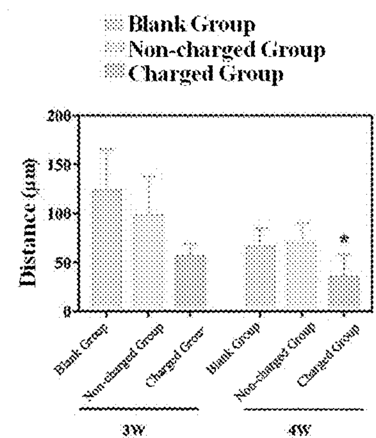

Histological results were as shown in FIGS. 8A and 8B, in which the red line was marked as the cemento-enamel junction (CEJ), the purple line represented the alveolar bone (AB), the blue line represented the attachment level to the junctional epithelium, and the green line represented the bone level. FIG. 8A showed the HE staining of mouse periodontium at 3 week and 4 week after the membrane was placed, which showed that compared with the blank group and non-charged group, the inflammatory cell infiltration was significantly reduced (the inflammatory cells were indicated by the black arrows) and the bone level was also better in the connective tissue (CT) of the High-charged group HC. The attachment level was significantly improved. The results of the attachment loss were statistically analyzed. As shown in FIG. 8B, it could be seen that the periodontal attachment loss after treatment with the charged membrane was significantly less than that in the blank group and the non-charged group.

4. Experiment on Breathability

A C360M water vapor permeability test system was used to test the water vapor permeance of the resulting dressing under the test conditions of 38° C. and 90% RH, with the observation focused on the water vapor permeance.

5. Piezoelectric Constant

A ZJ-3AN quasi-static $d_{33}$ meter was used to test the piezoelectric constant of the dressing.

TABLE 3A

| | Example 5A (ZnO) | | | Comparative Example 1A | | | Comparative Example 2A | | |
|---|---|---|---|---|---|---|---|---|---|
| Ferroelectric material | KNN | BTO | BST | KNN | BTO | BST | KNN | BTO | BST |
| Piezoelectric constant (pc/V) | 18 | 21 | 20 | 11 | 17 | 9 | 7 | 13 | 5 |
| Water vapor permeance ($g/m^2 \cdot 24$ h) | 1554 | 1321 | 2079 | 1534 | 1352 | 2185 | 1531 | 1365 | 2105 |

(II) Preparation and Performance Test of Tissue Repair Membrane

Example 1B (1) Firstly, the ferroelectric polymer P(VDF-TrFE) was mixed at a ratio of 10 wt % with an organic solvent DMF at a temperature of 37° C. and stirred for 2 h to make it dissolved completely, thereby forming a ferroelectric polymer mixture.

(2) 10 wt % of inorganic particles ZnO (having an average particle size of 80 nm) were added to the ferroelectric polymer mixture obtained in step (1), stirred for 6 h or more or overnight to make them fully dissolved, and then subjected to ultrasonic shaking for 1 h to form a homogeneous dispersion.

(3) The dispersion obtained in step (2) was dumped on a glass plate washed with the first deionized water, anhydrous ethanol, and second deionized water and cast to form a membrane, and the membrane was scraped with a scraper. The membrane was dried at 60° C. for 4 h to completely volatilize the solvent and to obtain a polymer membrane.

(4) The primary membrane prepared in step (3) was immersed in a 37% hydrochloric acidic solution for 12 h or more.

(5) The membrane prepared in step (4) was removed, washed several times with deionized water, taken out, and purged at 37° C. for 3 h to obtain the polymer membrane.

(6) The polymer membrane prepared in step (5) was subjected to annealing treatment at 90° C. for 15 min. Thereafter, the resulting membrane material was placed on the sample stage of a corona poling device for poling treatment. The parameters for poling were as follows: the polarization medium was air, the polarization voltage was 21 kV, the distance between the electrode tip and the sample was set to 15 mm, the polarization temperature was 37° C., and the polarization time was 30 min. A biomimetic electroactive breathable membrane was therefore obtained.

The main component of the tissue repair membrane with both breathability and electroactivity obtained by the above steps was a ferroelectric polymer—polyvinylidene fluoride (PVDF), and the thickness of the membrane was 50 μm.

A C360M water vapor permeability test system was used to test the water vapor permeance of the resulting tissue repair membrane with both breathability and electroactivity under the test conditions of 38° C. and 90% RH, with the observation focused on the water vapor permeance of the tissue repair membrane.

The resulting tissue repair membrane with both breathability and electroactivity was implanted into the skull defect site of a rat. The charged dense membrane (subjected to the treatment with inorganic particles and the subsequent annealing treatment, without the acid treatment) was used as the control group. Four weeks after the operation, the material was removed for the micro-CT observation and analysis, focusing on the repair and regeneration of the critical bone defect in skull.

Example 2B (1) Firstly, the ferroelectric polymer P(VDF-TrFE) was mixed at a ratio of 15 wt % with an organic solvent DMF at a temperature of 37° C. and stirred for 4 h to make it dissolved completely, thereby forming a ferroelectric polymer mixture.

(2) 8 wt % of inorganic particles ZnO (having an average particle size of 60 nm) was added to the ferroelectric polymer mixture obtained in step (1), stirred for 18 h to make them fully dissolved, and then subjected to ultrasonic shaking for 2 h to form a homogeneous dispersion.

(3) The dispersion obtained in step (2) was dumped on a glass plate washed with acetone and cast to form a membrane, and the membrane was scraped with a scraper. The membrane was dried at 40° C. for 6 h to completely volatilize the solvent and to obtain a polymer membrane.

(4) The primary membrane prepared in step (3) was immersed in a 30% hydrochloric acidic solution for 12 h.

(5) The membrane prepared in step (4) was removed, washed several times with deionized water, taken out, and purged at 37° C. for 1 h to obtain the polymer membrane.

(6) The polymer membrane prepared in step (5) was subjected to annealing treatment at 100° C. for 20 min. Thereafter, the resulting membrane material was placed on the sample stage of a corona poling device for poling treatment. The parameters for poling were as follows: the polarization medium was air, the polarization voltage was 21 kV, the distance between the electrode tip and the sample was set to 18 mm, the polarization temperature was 50° C., and the polarization time was 15 min. A biomimetic electroactive breathable membrane was therefore obtained.

The main component of the biomimetic electroactive breathable membrane obtained by the above steps was a ferroelectric polymer—polyvinylidene fluoride (PVDF), and the thickness of the membrane was 100 μm.

The resulting biomimetic electroactive breathable membrane with a porous structure was implanted into the skull defect site of a rat. The dense membrane (identical with that in Example 1B) was used as the control group. Four weeks after the operation, the material was removed for the micro-CT observation and analysis, focusing on the repair and regeneration of the critical bone defect in skull.

Example 3B (1) Firstly, the ferroelectric polymer P(VDF-TrFE) was mixed at a ratio of 10 wt % with an organic solvent DMF at a temperature of 37° C. and stirred for 3 h to make it dissolved completely, thereby forming a ferroelectric polymer mixture.
(2) 10 wt % of inorganic particles ZnO (having an average particle size of 80 nm) were added to the ferroelectric polymer mixture obtained in step (1), stirred for 18 h to make them fully dissolved, and then subjected to ultrasonic shaking for 0.5 h to form a homogeneous dispersion.
(3) The dispersion obtained in step (2) was dumped on a glass plate washed with acetone and cast to form a membrane, and the membrane was scraped with a scraper. The membrane was dried at 50° C. for 6 h to completely volatilize the solvent and to obtain a polymer membrane.
(4) The primary membrane prepared in step (3) was immersed in a 20% hydrochloric acidic solution for 18 h.
(5) The membrane prepared in step (4) was removed, washed several times with deionized water, taken out, and purged at 37° C. for 2 h to obtain the polymer membrane.
(6) The polymer membrane prepared in step (5) was subjected to annealing treatment at 100° C. for 15 min. Thereafter, the resulting membrane material was placed on the sample stage of a corona poling device for poling treatment. The parameters for poling were as follows: the polarization medium was air, the polarization voltage was 21 kV, the distance between the electrode tip and the sample was set to 21 mm, the polarization temperature was 40° C., and the polarization time was 40 min. A biomimetic electroactive breathable membrane was therefore obtained.

The main component of the biomimetic electroactive breathable membrane obtained by the above steps was a ferroelectric polymer—polyvinylidene fluoride (PVDF), and the thickness of the membrane was 30 μm.

The resulting biomimetic electroactive breathable membrane was implanted into the skull defect site of a rat. The dense membrane (identical with that in Example 1B) was used as the control group. Four weeks after the operation, the material was removed for the micro-CT observation and analysis, focusing on the repair and regeneration of the critical bone defect in skull.

Example 4B (1) Firstly, the ferroelectric polymer P(VDF-TrFE) was mixed at a ratio of 30 wt % with an organic solvent DMF at a temperature of 37° C. and stirred for 6 h to make it dissolved completely, thereby forming a ferroelectric polymer mixture.
(2) 12 wt % of inorganic particles calcium carbonate (having an average diameter of 80 nm) were added to the ferroelectric polymer mixture obtained in step (1), stirred for 24 h to make them fully dissolved, and then subjected to ultrasonic shaking for 1 h to form a homogeneous dispersion.
(3) The dispersion obtained in step (2) was dumped on a glass plate washed with acetone and cast to form a membrane, and the membrane was scraped with a scraper. The membrane was dried at 50° C. for 8 h to completely volatilize the solvent and to obtain a polymer membrane.
(4) The primary membrane prepared in step (3) was immersed in a 40% hydrochloric acidic solution for 6 h.
(5) The membrane prepared in step (4) was removed, washed several times with deionized water, taken out, and purged at 37° C. for 0.5 h to obtain the polymer membrane with a porous structure.
(6) The polymer membrane prepared in step (5) was subjected to annealing treatment at 100° C. for 5 min. Thereafter, the resulting membrane material was placed on the sample stage of a corona poling device for poling treatment. The parameters for poling were as follows: the polarization medium was air, the polarization voltage was 21 kV, the distance between the electrode tip and the sample was set to 35 mm, the polarization temperature was 25° C., and the polarization time was 10 min. A biomimetic electroactive breathable membrane was therefore obtained.

The main component of the biomimetic electroactive breathable membrane obtained by the above steps was a ferroelectric polymer—polyvinylidene fluoride (PVDF), and the thickness of the membrane was 20 μm.

The resulting biomimetic electroactive breathable membrane with a porous structure was implanted into the skull defect site of a rat. The dense membrane (identical with that in Example 1B) was used as the control group. Four weeks after the operation, the material was removed for the micro-CT observation and analysis, focusing on the repair and regeneration of the critical bone defect in skull.

Comparative Example 1B

Compared with Example 1B, Comparative Example 1B had the following differences: 10 wt % of inorganic particles ZnO (having an average particle size of 100 nm) and ferroelectric polymer P(VDF-TrFE) were dispersed in an organic solvent DMF by magnetic stirring to form a homogenous dispersion, from which a membrane casting solution of the polymer was obtained after ultrasonic shaking; the resulting membrane casting solution of the polymer was coated and cast on a glass plate washed with acetone, and dried by heating, so as to completely volatilize the solvent and to obtain a polymer membrane; the polymer membrane was immersed in a 20% hydrochloric acidic solution for 18 h; after washing and drying, the resulting membrane material was placed on the sample stage of a corona poling device for poling treatment to obtain a biomimetic electroactive breathable membrane with a thickness of 30 μm.

A ZJ-3AN quasi-static $d_{33}$ meter was used to test the piezoelectric constant of the repair membrane. The results were as shown in FIG. 16. The results showed that the piezoelectric constant of the repair membrane obtained in Comparative Example 1B was 3.5 pC/N, which was much lower than the piezoelectric constant of the tissue repair membrane in Example 1B.

Comparative Example 2B

The repair membrane was prepared in the same manner as in Example 1B, except for raising the drying temperature to 90° C. and changing the drying time to 5 h in step (3).

Comparative Example 3B

The repair membrane was prepared in the same manner as in Example 1B, except for changing the average particle size of the inorganic particles to 200 nm.

TABLE 1B

| | Charged dense membrane | Example 1B | Comparative Example 1B | Comparative Example 2B | Comparative Example 3B |
|---|---|---|---|---|---|
| Water vapor permeance ($g/m^2 \cdot 24$ h) | 34.7141 | 1208.2532 | 2012.3481 | 459.6932 | 2716.7429 |
| $d_{33}$ (PC/N) | 9.6 | 10 | 3.5 | 9 | 3.0 |

(III) Preparation of Performance Test of poly(L-lactic acid) Nanofiber Membrane

Example 1C 0.49 g of poly(L-lactic acid) powder was weighed and added to 7 ml of trifluoroethanol, and stirred magnetically for 3 h until the powder was completely dissolved to a clear and uniform solution. 7 ml of the mixed solution was transferred into an electrospinning syringe with a 22 G special needle. The outlet of the needle and the roller receiver covered with an aluminum foil were connected to the high-voltage power supply of the spinning machine, respectively. The electrospinning equipment was turned on, and the positive voltage was adjusted to 10.57 kV, the negative voltage to 3.05 kV, the injection rate to 0.065 mm/min, the rotation speed of the roller receiver to 2800 rpm, and the distance from the needle to the roller receiver to 12 cm. The spinning was completed 8 h later. A membrane with an aluminum foil was put in an oven and dried at room temperature for 24 h, and then put in a heating platform. A first-step annealing temperature was set to 105° C. for 10 h. When the temperature dropped to room temperature, the membrane was taken out and peeled off from the aluminum foil. The membrane was put in the heating platform again. A second-step annealing temperature was set to 160° C. for 10 h. In the annealing process, the membrane was clamped with a heat-resistant quartz glass plate to prevent shrinkage. When the temperature dropped to room temperature, the membrane was taken out. The annealed membrane was subjected to corona poling treatment. The parameters included: polarization voltage 16 kV, polarization distance 15 mm, polarization temperature 25° C., and polarization time 30 min. Low-intensity pulsed ultrasound was loaded with the parameters of operating frequency 1 MHz and effective sound intensity 1 W/cm$^2$ in a manner of output pulse.

Example 2C 0.49 g of poly(L-lactic acid) powder was weighed and added to 7 ml of trifluoroethanol, and stirred magnetically for 3 h until the powder was completely dissolved to a clear and uniform solution. 7 ml of the mixed solution was transferred into an electrospinning syringe with a 22 G special needle. The outlet of the needle and the roller receiver covered with an aluminum foil were connected to the high-voltage power supply of the spinning machine, respectively. The electrospinning equipment was turned on, and the positive voltage was adjusted to 10.57 kV, the negative voltage to 3.05 kV, the injection rate to 0.065 mm/min, the rotation speed of the roller receiver to 300 rpm, and the distance from the needle to the roller receiver to 12 cm. The spinning was completed 8 h later. A membrane with an aluminum foil was put in an oven and dried at room temperature for 24 h, and then put in a heating platform. A first-step annealing temperature was set to 105° C. for 10 h. When the temperature dropped to room temperature, the membrane was taken out and peeled off from the aluminum foil. The membrane was put in the heating platform again. A second-step annealing temperature was set to 160° C. for 10 h. In the annealing process, the membrane was clamped with a heat-resistant quartz glass plate to prevent shrinkage. When the temperature dropped to room temperature, the membrane was taken out. The annealed membrane was subjected to corona poling treatment. The parameters included: polarization voltage 16 kV, polarization distance 15 mm, polarization temperature 25° C., and polarization time 30 min. Low-intensity pulsed ultrasound was loaded with the parameters of operating frequency 1 MHz and effective sound intensity 1 W/cm$^2$ in a manner of output pulse.

Example 3C 0.49 g of poly(L-lactic acid) powder was weighed and added to 7 ml of trifluoroethanol, and stirred magnetically for 3 h until the powder was completely dissolved to a clear and uniform solution. 7 ml of the mixed solution was transferred into an electrospinning syringe with a 22 G special needle. The outlet of the needle and the roller receiver covered with an aluminum foil were connected to the high-voltage power supply of the spinning machine, respectively. The electrospinning equipment was turned on, and the positive voltage was adjusted to 10.57 kV, the negative voltage to 3.05 kV, the injection rate to 0.065 mm/min, the rotation speed of the roller receiver to 2800 rpm, and the distance from the needle to the roller receiver to 12 cm. The spinning was completed 8 h later. A membrane with an aluminum foil was put in an oven and dried at room temperature for 24 h, and then put in a heating platform. A first-step annealing temperature was set to 105° C. for 10 h. When the temperature dropped to room temperature, the membrane was taken out and peeled off from the aluminum foil. The membrane was put in the heating platform again. A second-step annealing temperature was set to 160° C. for 10 h. In the annealing process, the membrane was clamped with a heat-resistant quartz glass plate to prevent shrinkage. When the temperature dropped to room temperature, the membrane was taken out. The annealed membrane was subjected to corona poling treatment. The parameters included: polarization voltage 16 kV, polarization distance 15 mm, polarization temperature 25° C., and polarization time 30 min. The low-intensity pulsed ultrasound was not loaded. The low-intensity pulsed ultrasound was not loaded.

Example 4C 0.49 g of poly(L-lactic acid) powder was weighed and added to 7 ml of trifluoroethanol, and stirred magnetically for 3 h until the powder was completely dissolved to a clear and uniform solution. 7 ml of the mixed solution was transferred into an electrospinning syringe with a 22 G special needle. The outlet of the needle and the roller receiver covered with an aluminum foil were connected to the high-voltage power supply of the spinning machine, respectively. The electrospinning equipment was turned on, and the positive voltage was adjusted to 10.57 kV, the negative voltage to 3.05 kV, the injection rate to 0.065 mm/min, the rotation speed of the roller receiver to 300 rpm, and the distance from the needle to the roller receiver to 12 cm. The spinning was completed 8 h later. A membrane with an aluminum foil was put in an oven and dried at room temperature for 24 h, and then put in a heating platform. A first-step annealing temperature was set to 105° C. for 10 h. When the temperature dropped to room temperature, the membrane was taken out and peeled off from the aluminum foil. The membrane was put in the heating platform again. A second-step annealing temperature was set to 160° C. for 10 h. In the annealing process, the membrane was clamped with a heat-resistant quartz glass plate to prevent shrinkage. When the temperature dropped to room temperature, the membrane was taken out. The annealed membrane was subjected to corona poling treatment. The parameters included: polarization voltage 16 kV, polarization distance 15 mm, polarization temperature 25° C., and polarization time 30 min. The low-intensity pulsed ultrasound was not loaded.

Comparative Example 1C 0.49 g of poly(L-lactic acid) powder was weighed and added to 7 ml of trifluoroethanol, and stirred magnetically for 3 h until the powder was completely dissolved to a clear and uniform solution. 7 ml of the mixed solution was transferred into an electrospinning syringe with a 22 G special needle. The outlet of the needle and the roller receiver covered with an aluminum foil were connected to the high-voltage power supply of the spinning machine, respectively. The electrospinning equipment was turned on, and the positive voltage was adjusted to 10.57 kV, the negative voltage to 3.05 kV, the injection rate to 0.065 mm/min, the rotation speed of the roller receiver to 300 rpm, and the distance from the needle to the roller receiver to 12 cm. The spinning was completed 8 h later. A membrane with an aluminum foil was put in an oven and dried at room temperature for 24 h, and then put in a heating platform. A first-step annealing temperature was set to 105° C. for 10 h. When the temperature dropped to room temperature, the membrane was taken out and peeled off from the aluminum foil. The membrane was put in the heating platform again. A second-step annealing temperature was set to 160° C. for 10 h. In the annealing process, the membrane was clamped with a heat-resistant quartz glass plate to prevent shrinkage. When the temperature dropped to room temperature, the membrane was taken out. The low-intensity pulsed ultrasound was not loaded.

Comparative Example 2C 0.49 g of poly(L-lactic acid) powder was weighed and added to 7 ml of trifluoroethanol, and stirred magnetically for 3 h until the powder was completely dissolved to a clear and uniform solution. 7 ml of the mixed solution was transferred into an electrospinning syringe with a 22 G special needle. The outlet of the needle and the roller receiver covered with an aluminum foil were connected to the high-voltage power supply of the spinning machine, respectively. The electrospinning equipment was turned on, and the positive voltage was adjusted to 10.57 kV, the negative voltage to 3.05 kV, the injection rate to 0.065 mm/min, the rotation speed of the roller receiver to 300 rpm, and the distance from the needle to the roller receiver to 12 cm. The spinning was completed 8 h later. A membrane with an aluminum foil was put in an oven and dried at room temperature for 24 h, and then put in a heating platform. A first-step annealing temperature was set to 105° C. for 10 h. When the temperature dropped to room temperature, the membrane was taken out and peeled off from the aluminum foil. The membrane was put in the heating platform again. A second-step annealing temperature was set to 160° C. for 10 h. In the annealing process, the membrane was clamped with a heat-resistant quartz glass plate to prevent shrinkage. When the temperature dropped to room temperature, the membrane was taken out. The low-intensity pulsed ultrasound was not loaded.

Test Examples

1. Performance Test

The above treated poly(L-lactic acid) nanofiber membrane was tested for the piezoelectric coefficient and output voltage. The poly(L-lactic acid) nanofiber membrane was immersed in simulated body fluid for 7 days and tested for its remineralization performance by SEM and EDS.

2. Study on Promotion of Osteogenesis in rBMSCs by Low-Intensity Pulsed Ultrasound Response-Based poly(L-lactic acid) Nanofiber Membrane Biological experiments such as cell live/dead staining and cell adhesion were carried out to test that the low-intensity pulsed ultrasound response-based poly(L-lactic acid) nanofiber membrane had good biocompatibility. Moreover, rBMSCs were seeded on the poly(L-lactic acid) nanofiber membrane for 3, 7, and 14 days of low-intensity pulsed ultrasound response culture. Osteogenic indicators such as BMP2, OPN, and OCN were tested by PCR and immunofluorescence techniques to evaluate the osteogenic effect of the low-intensity pulsed ultrasound response-based poly(L-lactic acid) nanofiber membrane.

3. Study on Promotion of Healing in Critical Bone Defect by Low-Intensity Pulsed Ultrasound Response-Based poly(L-lactic acid) Nanofiber Membrane A 5-mm bone defect model of rat skull was constructed. At 4 week and 12 week after the poly(L-lactic acid) nanofiber membrane was implanted, the osteogenic effect was evaluated by micro-CT and tissue sections. On this basis, a mandible defect model of rat was designed and its application effect was evaluated.

4. Experimental Results

FIG. 17 showed the results of the XRD and FTIR tests for the PLLA nanofiber membrane, suggesting that after the annealing treatment and poling treatment, the crystal form of the material was more stable and the degree of orientation of the crystal increased. XRD showed an increase in (200) & (110) and a decrease in (111), indicating the presence of β phase. In the FTIR spectrum, the piezoelectricity of PLLA was highly dependent on the response of the dipole on the carbon-oxygen double bond to external pressure and an electric field. This result showed that the C═O peak in the Aligned group after annealing and poling was higher than those in the remaining groups.

FIG. 18 showed the indicator BMP2 detected by the immunofluorescence technique. UPR represented an unpolarized random (Random) membrane, UPA represented an unpolarized aligned (Aligned) membrane, PR represented a polarized random membrane, PA represented a polarized aligned membrane, and US represented ultrasonic treatment.

FIG. 19 showed the remineralization performance of the PLLA nanofiber membrane tested by SEM and EDS.

While the present disclosure has been described with reference to the exemplary embodiments, it shall be appreciated that the present disclosure is not limited to those disclosed exemplary embodiments. Various modifications or variations may be made to the exemplary embodiments described herein without departing from the scope or spirit of the present disclosure. The scope of the claims shall be given the broadest interpretation to cover all modifications and equivalent structures and functions.

The invention claimed is:

1. A method for preparing a medical material, wherein the method comprises the following steps:

(1) preparing a precursor material from a ferroelectric polymer and an inorganic pore-forming agent having a particle size of 40-100 nm, and a ferroelectric ceramic particle, wherein the precursor material is formed into a membrane by membrane casting and drying at 30° C. to 75° C. for 10 min to 24 h, the inorganic pore-forming agent is at least one of zinc oxide or calcium carbonate, the ferroelectric ceramic particle is selected from the group consisting of barium titanate, potassium sodium niobate, barium strontium titanate, and mixtures thereof; and (2) subjecting the membrane to annealing treatment, corona poling treatment, acid treatment to obtain a breathable polymer membrane, and optionally to ultrasonic treatment, wherein the annealing treatment is conducted at 80° C. to 150° C. for a period of from 5 min to 2 h.

2. The preparation method for the medical material according to claim 1, wherein conditions for the annealing treatment comprise treatment in air or vacuum at a temperature of 80° C. to 100° C. for 5 to 30 min, followed by natural cooling.

3. The preparation method for the medical material according to claim 1, wherein conditions for the corona poling treatment comprise polarization field strength of 0.1 kV/mm to 30 kV/mm, polarization time of 1 min to 60 min, a polarization medium being air, methyl silicone oil or vacuum, and a polarization temperature of 25° C. to 100° C.

4. The preparation method for the medical material according to claim 1, wherein the acid treatment comprises treatment for 3 to 30 h;

wherein the acidic solution is selected from aqueous solutions of hydrochloric acid, sulfuric acid, nitric acid, and carbonic acid, and a concentration of acid in the acidic solution is from 1% to 50%.

5. The preparation method for the medical material according to claim 1, wherein the ultrasonic treatment is low-intensity ultrasound.

6. The preparation method for the medical material according to claim 1, wherein the method comprises:

preparing a composite material from a ferroelectric polymer, a ferroelectric ceramic particle, and an inorganic pore-forming agent; and subjecting the composite material to annealing treatment, corona poling treatment, and acid treatment, successively; or to corona poling treatment, annealing treatment, and acid treatment, successively.

7. The preparation method for the medical material according to claim 1, wherein the method comprises the following steps:

(1) dissolving a ferroelectric polymer into an organic solvent to form a ferroelectric polymer mixture;

(2) adding zinc oxide and/or calcium carbonate, and barium titanate to the ferroelectric polymer mixture and mixing to form a dispersion;

(3) preparing a membrane from the dispersion by membrane casting to obtain a primary membrane, and immersing the primary membrane into an acidic solution for treatment to obtain a breathable polymer membrane; and (4) subjecting the breathable polymer membrane to the annealing treatment at 80° C. to 100° C. for 5 to 30 min, then to natural cooling at room temperature, and subsequently to the corona poling treatment, thereby obtaining a composite membrane with both breathability and electroactivity.

8. The preparation method for the medical material according to claim 1, wherein the ultrasound has an effective sound intensity of from 0.20 to 2.50 W/cm$^2$; the ultrasound has an ultrasonic frequency of from 0.5 to 4 MHz.

9. The preparation method for the medical material according to claim 1, wherein the ultrasound is continuous ultrasound or pulsed ultrasound.

* * * * *